United States Patent
Jain

(10) Patent No.: US 12,404,555 B2
(45) Date of Patent: *Sep. 2, 2025

(54) CRENOLANIB FOR TREATING FLT3 MUTATED PROLIFERATIVE DISORDERS ASSOCIATED MUTATIONS

(71) Applicant: Arog Pharmaceuticals, Inc., Plano, TX (US)

(72) Inventor: Vinay K. Jain, Dallas, TX (US)

(73) Assignee: Arog Pharmaceuticals, Inc., Plano, TX (US)

( * ) Notice: Subject to any disclaimer, the term of this patent is extended or adjusted under 35 U.S.C. 154(b) by 100 days.

This patent is subject to a terminal disclaimer.

(21) Appl. No.: 17/355,468

(22) Filed: Jun. 23, 2021

(65) Prior Publication Data

US 2021/0324481 A1    Oct. 21, 2021

Related U.S. Application Data

(63) Continuation of application No. 15/799,684, filed on Oct. 31, 2017, now Pat. No. 11,078,541.

(60) Provisional application No. 62/416,475, filed on Nov. 2, 2016.

(51) Int. Cl.
　　*C12Q 1/6886*　　(2018.01)
　　*A61K 31/4709*　　(2006.01)
　　*A61K 45/06*　　(2006.01)
　　*G01N 33/574*　　(2006.01)

(52) U.S. Cl.
　　CPC ........ *C12Q 1/6886* (2013.01); *A61K 31/4709* (2013.01); *A61K 45/06* (2013.01); *G01N 33/57492* (2013.01); *C12Q 2600/106* (2013.01); *C12Q 2600/118* (2013.01); *C12Q 2600/156* (2013.01); *G01N 2333/912* (2013.01)

(58) Field of Classification Search
　　None
　　See application file for complete search history.

(56) References Cited

U.S. PATENT DOCUMENTS

| | | | |
|---|---|---|---|
| 5,990,146 A | 11/1999 | Boschelli et al. | |
| 7,071,337 B2 | 7/2006 | Kath et al. | |
| 7,183,414 B2 | 2/2007 | Tom et al. | |
| 9,101,624 B2 | 8/2015 | Jain | |
| 9,393,240 B2 | 7/2016 | Jain | |
| 9,480,683 B2 | 11/2016 | Jain | |
| 9,801,870 B2 | 10/2017 | Jain | |
| 11,078,541 B2 * | 8/2021 | Jain ................. | G01N 33/57492 |
| 2004/0049032 A1 | 3/2004 | Charrier et al. | |
| 2005/0124599 A1 | 6/2005 | Kath et al. | |
| 2015/0031641 A1 | 1/2015 | Levine et al. | |

FOREIGN PATENT DOCUMENTS

| | | |
|---|---|---|
| WO | 1999016755 | 4/1999 |
| WO | 2001040217 A1 | 6/2001 |
| WO | 2002032861 A2 | 4/2002 |
| WO | 2002092599 A1 | 11/2002 |
| WO | 2003024931 A1 | 3/2003 |
| WO | 2003024969 A1 | 3/2003 |
| WO | 2003099771 A2 | 4/2003 |
| WO | 2003035009 A2 | 5/2003 |
| WO | 2003037347 A1 | 5/2003 |
| WO | 2003057690 A1 | 7/2003 |
| WO | 2004005281 A1 | 1/2004 |
| WO | 2004016597 A2 | 2/2004 |

(Continued)

OTHER PUBLICATIONS

Ostroverkhova et al. Trends in Molecular Medicine. 29(7): 554-566 (Year: 2023).*

Abu-Duhier, et al. "FLT3 internal tandem duplication mutations in adult acute myeloid leukemia define a high risk group" British Journal of Haematology. Jun. 7, 2000;111:190-195.

Amin, et al. "Having a higher blast percentage in circulation than bone marrow: clinical implications in myelodysplastic syndrome and acute lymphoid and myeloid leukemias" Leukemia. Jul. 28, 2005; 19: 1567-72.

(Continued)

*Primary Examiner* — Carla J Myers
(74) *Attorney, Agent, or Firm* — Edwin S. Flores; Daniel J. Chalker; Chalker Flores, LLP

(57) ABSTRACT

The present invention includes methods for treating a FLT3 mutated proliferative disorder comprising: measuring expression of a mutated FLT3 and one or more genetic abnormalities in a sample obtained from a tumor sample obtained from the patient, wherein the presence of the one or more genetic abnormalities indicates that the patient has a poor prognosis; and administering to the patient a therapeutically effective amount of crenolanib or a pharmaceutically acceptable salt thereof, wherein the crenolanib increases a chance of survival of the patient having both the mutated FLT3 and the one or more genetic abnormalities, wherein the crenolanib, as shown below, is administered to a subject suffering from said disorder:

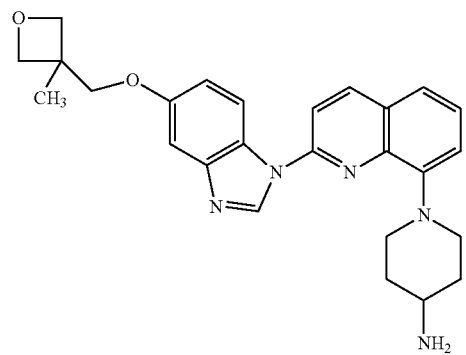

5 Claims, No Drawings

(56) References Cited

FOREIGN PATENT DOCUMENTS

| WO | 2004018419 A2 | 3/2004 |
| WO | 2004039782 A1 | 5/2004 |
| WO | 2004043389 A2 | 5/2004 |
| WO | 2004046120 A2 | 7/2004 |
| WO | 2004058749 A1 | 7/2004 |
| WO | 2014107209 | 7/2014 |
| WO | 2014107209 A2 | 7/2014 |
| WO | 2018085292 | 5/2018 |

OTHER PUBLICATIONS

Bacher, et al. "Prognostic relevance of FLT3-TKD mutations in AML: the combination matters-an analysis of 3082 patients" Blood. Mar. 1, 2008;111:2527-2537.

Borthakur, et al. "Phase I study of sorafenib in patients with refractory or relapsed acute leukemias. Haematologica" Jan. 2011; 96: 62-8. Epub Oct. 15, 2010.

Cheson, et al. "Revised Recommendations of the International Working Group for Diagnosis, Standardization of Response Criteria, Treatment Outcomes, and Reporting Standards for Therapeutic Trials in Acute Myeloid Leukemia" J Clin Oncol. Dec. 15, 2003; 21: 4642-4649.

ClinicalTrials.gov (NCT01522469) first received Jan. 30, 2012, 3 pp.

Cortes, et al. "AC220, a potent, selective, second generation FLT3 receptor tyrosine kinase (RTK) inhibitor, in a first-in-human (FIH) phase I AML study" Blood (ASH Annual Meeting Abstracts) Nov. 2009.

Cortes, et al. "A phase II open-label, AC220 monotherapy efficacy study in patients with refractory/relapsed FLT3-ITD positive acute myeloid leukemia: updated interim results" Blood (ASH Annual Meeting Abstracts) Dec. 2011.

Drexler, et al. "Expression of FLT3 receptor and response to FLT3 ligand by leukemic cells" Leukemia. Apr. 10, 1996; 10:588-599. (Abstract Only).

Gilliland, et al. "The roles of FLT3 in hematopoiesis and leukemia. Blood" Sept. 1, 2002;100:1532-1542.

Griswold, et al. "Effects of MLN518, A Dual FLT3 and KIT Inhibitor, on Normal and Malignant Hematopoiesis" Blood. Nov. 2004; 104 (9): 2912-2918.

Kindler, et al. "FLT3 as a therapeutic target in AML: still challenging after all these years" Blood. Dec. 9, 2010;116:5089-102.

Kiyoi, et al. "Internal tandem duplication of FLT3 associated with leukocytosis in acute promyelocytic leukemia" Leukemia Study Group of the Ministry of Health and Welfare (Kohseisho). Leukemia. 1997;11:1447-1452.

Kiyoi, et al. "Internal Tandem duplication of the FLT3 gene is a novel modality of elongation mutation which causes constitutive activation of the product" Leukemia. 1998;12:1333-1337.

Kiyoi, et al. "Prognostic implication of FLT3 and N-RAS gene mutations in acute myeloid leukemia" Blood. May 1, 1999;93:3074-3080.

Korean Intellectual Property Office, International Search Report and Written Opinion for PCT/US2013/064821 dated Dec. 26, 2013, 5 pp.

Kottaridis, et al. "The presence of a FLT3 internal tandem duplication in patients with acute myeloid leukemia (AML) adds important prognostic information to cytogenetic risk group and response to the first cycle of chemotherapy: analysis of 854 patients from the United Kingdom Medical Research Council AML 10 and 12 trials" Blood. Sep. 15, 2001; 98:1742-1759.

Levis, et al. "A FLT3 tyrosine kinase inhibitor is selectively cytotoxic to acute myeloid leukemia blasts harboring FLT3 Internal tandem duplication mutations" Blood. Aug. 1, 2001; 98(3): 885-887.

Levis, et al. "Small Molecule FLT3 Tyrosine Kinase Inhibitors" Current Pharmaceutical Design. 2004, 10, 1183-1193.

Lewis, et al. "Phase I Study of the Safety, Tolerability, and Pharmacokinetics of Oral CP-868,596, a Highly Specific Platelet-Derived Growth Factor Receptor Tyrosine Kinase Inhibitor in Patients With Advanced Cancers" J Clin Oncol. Nov. 1, 2009; 27(31) p. 5262-5269.

Korean Intellectual Property Office, International Search Report and Written Opinion for PCT/US2017/059377 dated Oct. 31, 2017, 21 pp.

Martin, et al. "Genomics in acute myeloid leukemia: from identification to personalization" Rhode Island Medical Journal, 2015, vol. 98, No. 11, pp. 27-30.

O'Donnell, et al. "Acute myeloid leukemia" Journal of the National Comprehensive Cancer Network, 2011, vol. 9, No. 3, pp. 280-317.

Thangavelu, et al. "Complete molecular risk stratification of de novo acute myeloid leukemia with intermediate cytogenetics using a nine-gene panel", Blood Journal, American Society of Hematology, 2014, vol. 124, No. 21, p. 2333.

Welsh, et al. "Bioinformatics analysis to determine prognostic mutations of 72 de novo acute myeloid leukemia cases from the Cancer Genome Atlas (TCGA) with 23 most common mutations and no abnormal cytogentics" Annals of Clinical & Laboratory Science, 2015, vol. 45, No. 5, pp. 515-521.

Arber, et al. "The 2016 revision to the World Health Organization classification of myeloid neoplasms and acute leukemia" Blood, May 19, 2016. 127(20): p. 2391-405.

Arber, et al. "Initial Diagnostic Workup of Acute Leukemia: Guideline From the College of American Pathologists and the American Society of Hematology" Arch Pathol Lab Med, Oct. 2017. 141(10): p. 1342-1393.

Banescu, et al. "The Value of FLT3, NPM1 and DNMT3A Gene Mutation Analysis in Acute Myeloid Leukemia Diagnosis" Revista Romana de Medicina de Laborator, 2019. 27(3): p. 239-243.

Cancer Genome Atlas Research, et al., "Genomic and epigenomic landscapes of adult de novo acute myeloid leukemia" with Supplemental Appendix (116 pages), N Engl J Med, May 30, 2013. 368(22): p. 2059-74.

DiNardo, et al. "Acute Myeloid Leukemia: from Mutation Profiling to Treatment Decisions" Curr Hematol Malig Rep, 2019.

Ding, et al. "Clonal evolution in relapsed acute myeloid leukaemia revealed by whole-genome sequencing" Nature, Jan. 2012. 481(7382): p. 506-10.

European Patent Office, European Search Report for EP Appl. No. 1786388.6 dated Apr. 25, 2019, 13 pp.

Fischer, et al. "Phase IIB trial of oral Midostaurin (PKC412), the FMS-like tyrosine kinase 3 receptor (FLT3) and multi-targeted kinase inhibitor, in patients with acute myeloid leukemia and high-risk myelodysplastic syndrome with either wild-type or mutated FLT3" J Clin Oncol, Oct. 1, 2010. 28(28): p. 4339-45.

Galanis, et al. "Abstract 3660: Crenolanib: A next generation FLT3 Inhibitor" DOI: 10.1158/1538-7445 AM2012-3660, Published Apr. 15, 2012, Cancer Research, vol. 72, Issue 8 Supplement, Abstract Only.

Hirsch, et al. "Genetic hierarchy and temporal variegation in the clonal history of acute myeloid leukaemia" Nat Commun, published Aug. 18, 2016. 7: p. 12475.

Hirschorn, et al. "A Comprehensive Review of Genetic Association Studies" March/Apr. 2002, vol.=4, No. 2, 45-61.

Marcucci, et al. "Age-Related Prognostic Impact of Different Types of DNMT3A Mutations in Adults With Primary Cytogenetically Normal Acute Myeloid Leukemia" Journal of Clinical Oncology, vol. 30, No. 7, Mar. 1, 2012, 742-750.

McMahon, et al. "Clonal selection with Ras pathway activation mediates secondary clinical resistance to selective FLT3 inhibition in acute myeloid leukemia" Cancer Discov, 2019.

Metzeler, et al. "Spectrum and prognostic relevance of driver gene mutations in acute myeloid leukemia" Blood, Aug. 4, 2016. 128(5): p. 686-98.

Papaemmanuil, et al. "Genomic Classification and Prognosis in Acute Myeloid Leukemia"—Supplemental Appendix, N Engl J Med, 2016. 374 (23): 275 pages.

Podoltsev, et al. "Selecting initial treatment of acute myeloid leukaemia in older adults" Blood Reviews, 31, (2017) 46-62.

(56) References Cited

OTHER PUBLICATIONS

Randhawa, et al. "Results of a Phase II Study of Crenolanib in Relapsed/Refractory Acute Myeloid Leukemia Patients (Pts) with Activating FLT3 Mutations" Blood, 2014. 124(21): p. 389-389.
Tyner, et al. "Functional genomic landscape of acute myeloid leukaemia" Nature, 2018.
Wang, et al. "Safety Study of Crenolanib, a Type I FLT3 Inhibitor, with Cytarabine/Daunorubicin or Cytarabine/Idarubicin Induction and High-Does Cytarabine Consolidation in Newly Diagnosed FLT3+ Aml" Eha Learning Center, Jun. 10, 2016; 133174 Abstract Only.
Zhang, et al. "Association between increased mutation rates in DNMT3A and FLT3-ITD and poor prognosis of patients with acute myeloid leukemia" Experimental and Therapeutic Medicine, 2019.
Mead, et al. "FLT3 tyrosine kinase domain mutations are biologically distinct from and have a significantly more favorable prognosis than FLT3 internal tandem duplications in patients with acute myeloid leukemia" Blood. Apr. 24, 2007; 110: 1262.
Michael, et al. "Phase Ib study of CP-868,596, a PDGFR inhibitor, combined with docetaxel with or without axitinib, a VEGFR inhibitor" British Journal of Cancer (published online Oct. 19, 2010) 103, 1554-1561.
Murata, et al. "Selective cytotoxic mechanism of GTP-14564, a novel tyrosine kinase inhibitor in leukemia cells expressing a constitutively active Fms-like tyrosine kinase 3 (FLT3)" J Biol Chem. 2003; 278 (35): 32892-32898 [Epub Jun. 18, 2003].
Nakao, et al. "Internal tandem duplication of the FLT3 gene found in acute myeloid leukemia" Leukemia Dec. 10, 1996;10:1911-1918. (Abstract Only).
O'Farrell, et al. "SU11248 is a novel FLT3 tyrosine kinase inhibitor with potent activity in vitro and in vivo" Blood. May 2003; 101(9): 3597-3605.
Sclenk, et al. "Mutations and Treatment Outcome in Cytogenetically Normal Acute Myeloid Leukemia" NEJM. May 1, 2008; 358: 1909.
Schnittger, et al. "Analysis of FLT3 length mutations in 1003 patients with acute myeloid leukemia: correlation to cytogenetics, FAB subtype, and prognosis in the AMLCG study and usefulness as a marker for the detection of minimal residual disease" Blood. Feb. 28, 2002;100:59-66.
Small, Donald "FLT3 mutations: biology and treatment" Hematology Am Soc Hematol Educ Program. 2006: 178-84.
Smith, et al. "Single agent CEP-701, a novel FLT3 inhibitor, shows biologic and clinical activity in patients with relapsed or refractory acute myeloid leukemia" Blood. May 2004; 103: 3669-3676.
Stirewalt, et al. "The role of FLT3 in hematopoietic malignancies" Nat Rev Cancer Sep. 2003;3:650-665.
Stone, et al. "PKC-412 FLT3 inhibitor therapy in AML: results of a phase II trials" Ann Hematol. 2004; 83 Suppl 1: S89-90.
Takahashi, Shinichiro "Downstream molecular pathways of FLT3 in the pathogenesis of acute myeloid leukemia biology and therapeutic implications" Journal of Hematology & Oncology, 2011, 4:13.
Thiede, et al. "Analysis of FLT3-activating mutations in 979 patients with acute myelogenous leukemia: association with FAB subtypes and identification of subgroups with poor prognosis" Blood. Jun. 15, 2002;99:4326-4335.
Tse, et al. "Inhibition of FLT3-mediated transformation by use of a tyrosine kinase inhibitor" Leukemia. Jul. 2001; 15(7): 1001-1010.
Yamamoto, et al. "Activating mutation of D835 within the activation loop of FLT3 in human hematologic malignancies" Blood. Apr. 15, 2001;97:2434-2439.
Yee, et al. "SU5416 and SU5614 inhibit kinase activity of wild-type and mutant FLT3 receptor tyrosine kinase" Blood. Oct. 2002; 100(8): 2941-2949.
Bains, et al. "FLT3 and NPM1 mutations in myelodysplastic syndromes: Frequency and potential value for predicting progression to acute myeloid leukemia" American Journal of Clinical Pathology. Jan. 2011; 135: 62-69.
Bakshi, S., et al. "Trisomy 8 in leukemia: A GCRI experience," Indian J Hum Genet. 2012;18:106-108.

ClinicalTrials.gov (NCT01657682).
ClinicalTrials.gov (NCT02283177).
ClinicalTrials.gov (NCT02400281).
ClinicalTrials.gov (NCT02626338).
Dicker, et al. "Trisomy 13 is strongly associated with Aml 1/RUNX1 mutations and increased FLT3 expression in acute myeloid leukemia," Blood. 2007;110:1308-1316.
Döhner, et al. "Diagnosis and management of AML in adults: 2017 ELN recommendations from an international expert panel," Blood. vol. 129, No. 3, pp. 424-447 (Nov. 28, 2016).
Herold, et al. "Isolated trisomy 13 defines a homogeneous AML subgroup with high frequency of mutations in spliceosome genes and poor prognosis," Blood. 2014;124:1304-1311.
Levis, et al. "Results from a randomized trial of salvage chemotherapy followed by lestaurtinib for patients with FLT3 mutant AML in first relapse," Blood. 2011;117:3294-3301.
Mendler, J., "RUNX1 Mutations Are Associated With Poor Outcome in Younger and Older Patients With Cytogenetically Normal Acute Myeloid Leukemia and With Distinct Gene and MicroRNA Expression Signatures," J. Clin. Oncol. vol. 30, No. 25, pp. 3109-3118 (Jul. 2, 2012).
Papaemmanuil, E., "Genomic Classification and Prognosis in Acute Myeloid Leukemia," New England J. Med. vol. 374, No. 23, pp. 2209-2221 (Jun. 9, 2016).
Paschka, et al. "Wilms' Tumor 1 Gene Mutations Independently Predict Poor Outcome in Adults With Cytogenetically Normal Acute Myeloid Leukemia: A Cancer and Leukemia Group B Study," J Clin Oncol. 2008;26:4595-4602.
Vanderwalde, A., "Genetics of Acute Myeloid Leukemia," available at http://emedicine.medscape.com/ article/1936033-overview (last updated Apr. 1, 2016).
Bhamidpati, et al. FLT3 mutations in myelodysplastic syndromes (MDS) and chronic myelomonocytic leukemia (CMML). 2012. Journal of Clinical Oncology. Suppl; abstract 6597.
Fitchen, et al. "Genetically Engineered Protection Against Viruses in Transgenic Plants" (1993) Annu Rev. Microbiol. 47:739-764.
Genecards, "GeneCards for DNMT3A" available via URL: <genecards.org/cgi-bin/carddisp.pl?gene=DNMT3A >, printed on Feb. 4, 2020, pp. 1-30 (Year: 2020).
Hattersley, et al. "What makes a good genetic association study?" Genetic Epidemiology 5, Lancet, vol. 366, Oct. 8, 2005, 1315-1323.
Randhawa, et al. "Results of a Phase II Study of Crenolanib in Relapsed/Refractory Acute Myeloid Leukemia Patients with Activating FLT3 Mutations" Abstract Only, Blood, vol. 124, Issue 21 Blood Journal, Dec. 4, 2014, XP055570030.
Zhang, et al. "Clinical Resistance to Crenolanib in Acute Myeloid Leukemia Due to Diverse Molecular Mechanisms" Nature Communications, Jan. 2019, 10(1): 244, p. 1-13.
Ahsan, et al. "Mechanism of Resistance to EGFR Tyrosine kinase Inhibitors and Therapeutic Approaches : An Update" Adv Exp Med Biol, 2016.
Badar, et al. Detectable FLT3-ITD or RAS mutation at the time of transformation from MDS to AML predicts for very poor outcomes. Leuk Res Dec. 2015;39:1367-74.
Belchis, et al. "Heterogeity of resistance mutations detectable by next-generation sequencing in TKI-treated lung adenocarcinoma" Oncotarget, vol. 7. No 29, Jun. 2016.
Chabon, et al. "Circulating tumour DNA profiling reveals heterogeity of EGFR inhibitor resistance mechanisms in lung cancer patients" Nature Communications, Jun. 2016.
Ching, et al. Abstract Only LB-215 "Analysis of mutations associated with response to glasdegib in acute myeloid leukemia (AML) and myelodysplastic syndrome (MDS) " Cancer Research, 2018.
De Melo Galiato, et al. "Mechanisms of resistance and sensitivity to anti-HER2 therapies and anti-HER2 breast cancer" Oncotarget, vol. 7, No. 39. Jan. 2016.
Dohner, et al., "Diagnosis and management of AML in adults: 2017 ELN recommendations from an international expert panel" Blood, Jan. 26, 2017. 129(4): p. 424-447.
Engleman, et al. "MET Amplification Leads Gefitinib Resistance in Lung by activating ERBB3 Signaling" Science, May 2007.

(56) References Cited

OTHER PUBLICATIONS

Grunwald, et al. "FLT3 inhibitors for acute myeloid leukemia: a reviw for their efficacy and mechanisms of resistance" International Journal of Hematology, 2013.

Heidel, et al. "Clinical resistance to kinase inhibitor PKC412 in acute myeloid leukemia by mutation of Asn-676 in the FLY3 tyrosine kinase domian" Neoplasia, Jan. 1, 2006.

Ho, et al. "Acquired BRAF V600E Mutation as Resistant Mechanism after Treatment with Osimertinib" Journal of Thoracic Oncology, 2016.

Hocchaus, et al. "Molecular and and chromosomal mechanisms of resistance to Imatinib (STI571) therapy" Leukemia, 2002.

Hong, et al. "Src Mutation Induces Acquired Lapatinib Resistance in ERBB2-Amplified Human Gastroesophageal Adenocarcinoma Models" PLOS One, Oct. 2014.

Indian Patent Office, Examination Report for India Patent Appl. No. 201917020799, dated Sep. 30, 2021.

Japan Patent Office, Examination Report for Japan Patent Appl No. 2018-506309, dated Apr. 6, 2021, 6 pp.

Katayama, et al. "Mechanisms of acquired crizotinib resistance in ALK-rearranged lung cancer" Science Translational Medicine, Feb. 2012.

Klco, et al. "Functional heterogeneity of genetically defined subclones in acute myeloid leukemia" Cancer Cell, Mar. 17, 2014.

Martin, et al., "Genomics in actue myeloid luekemia: from identification to personalization", Rhode Island Medical Journal, Nov. 2015, vol. 98, No. 11, pp. 27-30.

Mendler, et al., "RUNX1 mutations are associated with poor outcome in younger and older patients with cytogenetically normal acute myeloid leukemia and with distinct gene and MicroRNA expression signatures" J Clin Oncol, Sep. 1, 2012. 30(25): p. 3109-18.

Nakagawa, et al., "EGFR-TKI resistance due to BIM polymorphism can be circumvented in combination with HDAC Inhibition" Cancer Res, Apr. 2013. 73(8): p. 2428-34.

Nazarian, et al., "Melanomas acquire resistance to B-RAF(V600E) inhibition by RTK or N-RAS upregulation" Nature, Dec. 16, 2010. 468(7326): p. 973-7.

Odonnell, et al., "Acute myeloid leukemia", Journal of the National Comprehensive Cancer Network, Mar. 2011, vol. 9, No. 3, pp. 280-317.

Papadimitrikopoulou, et al., "LBA51Analysis of resistance mechanisms to osimertinib in patients with EGFR T790M advanced NSCLC from the AURA3 study" Abstract Only, Annals of Oncology, 2018. 29(suppl_8).

Paschka, et al., "Wilms tumor 1 gene mutations independently predict poor outcome in adults with cytogenetically normal acute myeloid leukemia: a cancer and leukemia group B study" J Clin Oncol, Oct. 1, 2008. 26(28): p. 4595-602.

Patel, et al. "Prognostic relevance of integrated genetic profiling in acute myeloid leukemia" N Engl J Med, Mar. 22, 2012;366:1079-89.

Piccaluga, et al., "Imatinib mesylate in the treatment of hematologic malignancies" Expert Opin Biol Ther, 2007. 7(10): p. 1597-611.

Quentmeier, et al., "BCR-ABL1-independent PI3Kinase activation causing imatinib-resistance" J Hematol Oncol, 2011. 4: p. 6.

Slany, et al. "The molecular Biology of Mixed Lineage Leukemia" Hematologica, 2009.

Smith, et al., "FLT3 D835 mutations confer differential resistance to type II FLT3 inhibitors" Leukemia, 2015. 29(12): p. 2390-2, accepted article preview online Jun. 25, 2015.

Smith, et al., "Validation of ITD mutations in FLT3 as a therapeutic target in human acute myeloid leukaemia" Nature, 2012. 485(7397): p. 260-3.

Wagle, et al., "Dissecting Therapeutic Resistance to RAF Inhibition in Melanoma by Tumor Genomic Profiling" Journal of Clinical Oncology, Aug. 2011. 29(22): p. 3085-3096.

Weisberg, et al., "Drug resistance in mutant FLT3-positive AML" Oncogene, 2010. 29(37): p. 5120-34, published online Jul. 12, 2010.

Welsh et al: "Bioinformatics analysis to determine prognostic mutations of 72 de novo acute myeloid leukemia cases from the cancer genome atlas with 23 most common mutations and no abnormal cytogenetics", Annals of Clinical and Laboratory Science, 45(5), Jan. 1, 2015, pp. 515-521.

Woyach, et al., "Resistance mechanisms for the Brutons tyrosine kinase inhibitor ibrutinib" N Engl J Med, Jun. 2014. 370(24): p. 2286-94.

Zorn, et al. "Crystal Structure of the FLT3 Kinase DomainBound to the Inhibitor Quizartinib (AC220)" Plos One, Apr. 2, 2015.

\* cited by examiner

CRENOLANIB FOR TREATING FLT3 MUTATED PROLIFERATIVE DISORDERS ASSOCIATED MUTATIONS

CROSS-REFERENCE TO RELATED APPLICATIONS

This application is a continuation of U.S. patent application Ser. No. 15/799,684, filed Oct. 31, 2017, which claims priority to U.S. Provisional Application Ser. No. 62/416,475, filed Nov. 2, 2016, the entire contents of which are incorporated herein by reference.

STATEMENT OF FEDERALLY FUNDED RESEARCH

Not applicable.

TECHNICAL FIELD OF THE INVENTION

The present invention relates in general to the use of crenolanib in a pharmaceutically acceptable salt form for the treatment of proliferative disorder(s), characterized by mutations to particular tyrosine kinase pathways, and to a method of treatment of warm-blooded animals, preferably humans, in which a therapeutically effective dose of crenolanib is administered to a subject suffering from said proliferative disorder.

INCORPORATION-BY-REFERENCE OF MATERIALS FILED ON COMPACT DISC

Not applicable.

BACKGROUND OF THE INVENTION

Without limiting the scope of the invention, its background is described in connection with protein kinases.

Protein kinases are enzymes that chemically modify other proteins by catalyzing the transfer of gamma phosphates from nucleotide triphosphates, often adenosine triphosphate (ATP), and covalently attaching them to a free hydroxyl group of amino acid residues serine, threonine and tyrosine.

Approximately 30% of all human proteins may be modified by kinase activity. Protein kinases direct the enzymatic activity, cellular location and primary function/association of substrate proteins and regulate cell signal transduction and cell function coordination.

Research studies have shown that aberrant expression of normal or mutated protein kinases are frequently associated with the formation and propagation of a number of diseases. Studies have shown that overexpression or inappropriate protein kinase expression is associated with cancer, cardiovascular disease, rheumatoid arthritis, diabetes, ocular disease, neurologic disorders and autoimmune disease. Thus, investigating compounds that potently inhibit the activity and function of protein kinases will allow for a greater understanding of the physiological roles of protein kinases.

The FMS-like tyrosine kinase 3 (FLT3) gene encodes a membrane bound receptor tyrosine kinase that affects hematopoiesis leading to hematological disorders and malignancies. See Drexler, H G et al. Expression of FLT3 receptor and response to FLT3 ligand by leukemic cells. Leukemia. 1996; 10:588-599; Gilliland, D G and J D Griffin. The roles of FLT3 in hematopoiesis and leukemia. Blood. 2002; 100:1532-1542; Stirewalt, D L and J P Radich. The role of FLT3 in hematopoietic malignancies. Nat Rev Cancer. 2003; 3:650-665. Activation of FLT3 receptor tyrosine kinases is initiated through the binding of the FLT3 ligand (FLT3L) to the FLT3 receptor, also known as Stem cell tyrosine kinase-1 (STK-1) and fetal liver kinase-2 (flk-2), which is expressed on hematopoietic progenitor and stem cells.

FLT3 is one of the most frequently mutated genes in hematological malignancies, present in approximately 30% of adult acute myeloid leukemias (AML). See Nakao M, S Yokota and T Iwai. Internal tandem duplication of the FLT3 gene found in acute myeloid leukemia. Leukemia. 1996; 10:1911-1918; H Kiyoi, M Towatari and S Yokota. Internal Tandem duplication of the FLT3 gene is a novel modality of elongation mutation, which causes constitutive activation of the product. Leukemia. 1998; 12:1333-1337; P D Kottaridis, R E Gale, et al. The presence of a FLT3 internal tandem duplication in patients with acute myeloid leukemia (AML) adds important prognostic information to cytogenetic risk group and response to the first cycle of chemotherapy: analysis of 854 patients from the United Kingdom Medical Research Council AML 10 and 12 trials. Blood. 2001; 98:1742-1759; Yamamoto Y, Kiyoi H, Nakano Y. Activating mutation of D835 within the activation loop of FLT3 in human hematologic malignancies. Blood. 2001; 97:2434-2439; Thiede C, C Steudel, Mohr B. Analysis of FLT3-activating mutations in 979 patients with acute myelogenous leukemia: association with FAB subtypes and identification of subgroups with poor prognosis. Blood. 2002; 99:4326-4335. FLT3 mutations have been detected in approximately 2% of patients diagnosed with intermediate and high risk myelodysplastic syndrome (MDS). See S Bains, Luthra R, Medeiros L J and Zuo Z. FLT3 and NPM1 mutations in myelodysplastic syndromes: Frequency and potential value for predicting progression to acute myeloid leukemia. American Journal of Clinical Pathology. January 2011; 135:62-69; P K Bhamidipati, Daver N G, Kantarjian H, et al. FLT3 mutations in myelodysplastic syndromes (MDS) and chronic myelomonocytic leukemia (CMML). 2012. Journal of Clinical Oncology. Suppl; abstract 6597. Like MDS, the number of FLT3 mutations in patients with acute promyelocytic leukemia (APL) is small. The most common FLT3 mutations are internal tandem duplications (ITDs) that lead to in-frame insertions within the juxtamembrane domain of the FLT3 receptor. FLT3-ITD mutations have been reported in 15-35% of adult AML patients. See Nakao M, S Yokota and T Iwai. Internal tandem duplication of the FLT3 gene found in acute myeloid leukemia. Leukemia. 1996; 10:1911-1918; H Kiyoi, M Towatari and S Yokota. Internal Tandem duplication of the FLT3 gene is a novel modality of elongation mutation, which causes constitutive activation of the product. Leukemia. 1998; 12:1333-1337; H Kiyoi, T Naoe and S Yokota. Internal tandem duplication of FLT3 associated with leukocytosis in acute promyelocytic leukemia. Leukemia Study Group of the Ministry of Health and Welfare (Kohseisho). Leukemia. 1997; 11:1447-1452; S Schnittger, C Schoch and M Duga. Analysis of FLT3 length mutations in 1003 patients with acute myeloid leukemia: correlation to cytogenetics, FAB subtype, and prognosis in the AMLCG study and usefulness as a marker for the detection of minimal residual disease. Blood. 2002; 100:59-66. A FLT3-ITD mutation is an independent predictor of poor patient prognosis and is associated with increased relapse risk after standard chemotherapy, and decreased disease free and overall survival. See F M Abu-Duhier, Goodeve A C, Wilson G A, et al. FLT3 internal tandem duplication mutations in adult acute myeloid leukemia define a high risk group. British Journal of Haematology. 2000; 111:190-195; H Kiyoi, T Naoe, Y Nakano, et al.

Prognostic implication of FLT3 and N-RAS gene mutations in acute myeloid leukemia. Blood. 1999; 93:3074-3080. Less frequent are FLT3 point mutations that arise in the activation loop of the FLT3 receptor. The most commonly affected codon is aspartate 835 (D835). Nucleotide substitutions of the D835 residue occur in approximately 5-10% of adult acute myeloid leukemia patients. See D L Stirewalt and J P Radich. The role of FLT3 in haematopoietic malignancies. Nature Reviews Cancer. 2003; 3:650-665; Y Yamamoto, H Kiyoi and Y Nakano, et al. Activating mutation of D835 within the activation loop of FLT3 in human hematologic malignancies. Blood. 2001; 97:2434-2439; C Thiede, Steudal C, Mohr B, et al. Analysis of FLT3-activating mutations in 979 patients with acute myelogenous leukemia: association with FAB subtypes and identification of subgroups with poor prognosis. Blood. 2002; 99:4326-4335; U Bacher, Haferlach C, W Kern, et al. Prognostic relevance of FLT3-TKD mutations in AML: the combination matters—an analysis of 3082 patients. Blood. 2008; 111:2527-2537.

The heightened frequency of constitutively activated mutant FLT3 in adult AML has made the FLT3 gene a highly attractive drug target in this tumor type. Several FLT3 inhibitors with varying degrees of potency and selectivity for the target have been or are currently being investigated and examined in AML patients. See T Kindler, Lipka D B, and Fischer T. FLT3 as a therapeutic target in AML: still challenging after all these years. Blood. 2010; 116:5089-102.

FLT3 kinase inhibitors known in the art include Lestaurtinib (also known as CEP 701, formerly KT-555, Kyowa Hakko, licensed to Cephalon); CHIR-258 (Chiron Corp.); EB10 and IMC-EB10 (ImClone Systems Inc.); Midostaurin (also known as PKC412, Novartis AG); Tandutinib (also known as MLN-518, formerly CT53518, COR Therapeutics Inc., licensed to Millennium Pharmaceuticals Inc.); Sunitinib (also known as SU11248, Pfizer USA); Quizartinib (also known as AC220, Ambit Biosciences); XL 999 (Exelixis USA, licensed to Symphony Evolution, Inc.); GTP 14564 (Merck Biosciences UK); AG1295 and AG1296; CEP-5214 and CEP-7055 (Cephalon). The following PCT International Applications and U.S. patent applications disclose additional kinase modulators, including modulators of FLT3: WO 2002032861, WO 2002092599, WO 2003035009, WO 2003024931, WO 2003037347, WO 2003057690, WO 2003099771, WO 2004005281, WO 2004016597, WO 2004018419, WO 2004039782, WO 2004043389, WO 2004046120, WO 2004058749, WO 2004058749, WO 2003024969 and U.S. Patent Application No. 2004/0049032. See also Levis M, KF Tse, et al. 2001 "A FLT3 tyrosine kinase inhibitor is selectively cytotoxic to acute myeloid leukemia blasts harboring FLT3 internal tandem duplication mutations." Blood 98(3): 885-887; Tse K F, et al., Inhibition of FLT3-mediated transformation by use of a tyrosine kinase inhibitor. Leukemia. July 2001; 15 (7): 1001-1010; Smith, B. Douglas et al., Single agent CEP-701, a novel FLT3 inhibitor, shows biologic and clinical activity in patients with relapsed or refractory acute myeloid leukemia Blood, May 2004; 103: 3669-3676; Griswold, Ian J. et al., Effects of MLN518, A Dual FLT3 and KIT Inhibitor, on Normal and Malignant Hematopoiesis. Blood, November 2004; 104 (9): 2912-2918 [Epub ahead of print July 8]; Yee, Kevin W. H. et al., SU5416 and SU5614 inhibit kinase activity of wild-type and mutant FLT3 receptor tyrosine kinase. Blood, October 2002; 100(8): 2941-2949; O'Farrell, Anne-Marie et al., SU11248 is a novel FLT3 tyrosine kinase inhibitor with potent activity in vitro and in vivo. Blood, May 2003; 101(9): 3597-3605; Stone, R. M et al., PKC-412 FLT3 inhibitor therapy in AML: results of a phase II trials. Ann. Hematol. 2004; 83 Suppl 1:S89-90; and Murata, K. et al., Selective cytotoxic mechanism of GTP-14564, a novel tyrosine kinase inhibitor in leukemia cells expressing a constitutively active Fms-like tyrosine kinase 3 (FLT3). J Biol Chem. Aug. 29, 2003; 278 (35): 32892-32898 [Epub 2003 Jun. 18]; Levis, Mark et al., Small Molecule FLT3 Tyrosine Kinase Inhibitors. Current Pharmaceutical Design, 2004, 10, 1183-1193.

The aforementioned inhibitors have either been or are currently being investigated in the preclinical setting, or phase I and II trials as monotherapy in relapsed AML, or in phase III combination studies in relapsed AML. Despite reports of successful inhibition of FLT3 with these compounds in preclinical studies, complete remissions have rarely been achieved in FLT3 mutant AML patients in the clinical setting. For the majority of patients, the clinical response is short-lived. Response criteria for AML clinical trials are adapted from the International Working Group for AML. See Cheson et al. Revised Recommendations of the International Working Group for Diagnosis, Standardization of Response Criteria, Treatment Outcomes, and Reporting Standards for Therapeutic Trials in Acute Myeloid Leukemia. J Clin Oncol. 2003; 21: 4642-4649. Responders are patients who obtain a Complete Response (CR), Complete Response with incomplete blood count recovery (CRi), or Partial Remission (PR). Briefly, criteria are as follows:

1. Complete Remission (CR):
   a. Peripheral Blood Counts:
      i. No circulating blasts
      ii. Neutrophil count ≥1.0×10$^9$/L
      iii. Platelet count ≥100×10$^9$/L
   b. Bone marrow aspirate and biopsy:
      i. ≤5% blasts
      ii. No Auer Rods
      iii. No extramedullary leukemia
2. Complete Remission with Incomplete Blood Count Recovery (CRi):
   a. Peripheral blood counts:
      i. No circulating blasts
      ii. Neutrophil count <1.0×10$^9$/L, or
      iii. Platelet count <100×10$^9$/L
   b. Bone marrow aspirate and biopsy
      i. ≤5% blasts
      ii. No Auer Rods
      iii. No extramedullary leukemia
3. Partial Remission:
   a. All CR criteria if abnormal before treatment except:
   b. ≥50% reduction in bone marrow blast but still >5%

To date, clinical responses to FLT3 inhibitors have been primarily limited to clearance of peripheral blood (PB) blasts, which frequently return within a matter of weeks, while bone marrow (BM) blasts remain largely unaffected. For example, treatment with sorafenib, the prior mentioned multi-kinase inhibitor with activity against mutant FLT3, while effective in clearing PB blasts, has resulted in only modest BM blast reductions. See G Borthakur et al. Phase I study of sorafenib in patients with refractory or relapsed acute leukemias. Haematologica. January 2011; 96: 62-8. Epub 2010 Oct. 15. BM blast percentage plays a central role in the diagnosis and classification of AML. The presence of a heightened percentage of blasts in BM is associated with significantly shorter overall survival. See Small D. FLT3 mutations: biology and treatment. Hematology Am Soc Hematol Educ Program. 2006: 178-84; HM Amin et al. Having a higher blast percentage in circulation than bone marrow: clinical implications in myelodysplastic syndrome and acute lymphoid and myeloid leukemias. Leukemia. 2005; 19: 1567-72. To effectively treat FLT3 mutated AML patients and overcome the significant unmet need in this patient population, an inhibitor is required that significantly depletes both PB and BM blasts, bridges high risk and heavily pretreated patients to stem cell transplant, and can help to decrease relapse rates and increase overall survival in early stage disease patients.

Independent of the patient's FLT3 status, genetic abnormalities—including recurrent mutations, chromosomal aneuploidies and structural abnormalities—have historically played a critical role in characterizing the leukemia, helping determine disease aggressiveness, response to treatment, and prognosis. In the following table, "favorable risk" disease is associated with long-term survival of up to 65%, "intermediate risk" disease is associated with long-term survival of about 25%, and "adverse risk" disease is associated with long-term survival of less than 10%. See Vander-Walde, A., "Genetics of Acute Myeloid Leukemia," available at http://emedicine.medscape.com/article/1936033-overview (last updated 1 Apr. 2016).

| Risk Group | Genetic Abnormality |
| --- | --- |
| Favorable Risk | t(8; 21)(q22; q22.1); RUNX1-RUNX1T1 |
| | inv(16)(p13.1q22) or t(16; 16)(p13.1; q22); CBFB-MYH11 |
| | Mutated NPM1 without FLT3-ITD or with FLT3-ITD$^{low}$ |
| | Biallelic mutated CEBPA |
| Intermediate Risk | Mutated NPM1 and FLT3-ITD$^{high}$ |
| | Wild-type NPM1 without FLT3-ITD or with FLT3-ITD$^{low}$ (without adverse-risk genetic lesions) |
| | t(9; 11)(p21.3; q23.3); MLLT3-KMT2A |
| | Cytogenetic abnormalities not classified as favorable or adverse |
| Adverse Risk | t(6; 9)(p23; q34.1); DEK-NUP214 |
| | t(v; 11q23.3); KMT2A rearranged |
| | t(9; 22)(q34.1; q11.2); BCR-ABL1 |
| | inv(3)(q21.3q26.2) or t(3; 3)(q21.3; q26.2); GATA2, MECOM(EVI1) |
| | −5 or del(5q); −7; −17/abn(17p) |
| | Complex karyotype, monosomal karyotype |
| | Wild-type NPM1 and FLT3-ITD$^{high}$ |
| | Mutated RUNX1 |
| | Mutated ASXL1 |
| | Mutated TP53 |

See Döhner, H., et al. Diagnosis and management of AML in adults: 2017 ELN recommendations from an international expert panel. Blood. 2016; 129:424-447.

Additionally, in the context of AML, clinicians and researchers have recently begun a progressive shift away from a morphologic classification scheme to one informed by causative genomic changes. See Papaemmanuil, E., et al. Genomic Classification and Prognosis in Acute Myeloid Leukemia. N Engl J Med. 2016; 374:2209-2221. Notably, a recent analysis of 1540 AML patients revealed 5234 "driver mutations" (using widely accepted genetic criteria for cancer-associated genes) involving 76 genes or regions within those patients, with mutation frequencies consistent with those found in previous studies. These driver mutations included recurrent fusion genes, aneuploidies, and leukemia gene mutations (such as base substitutions and small (200-bp) insertions or deletions), all found to display an effect on individual patient prognosis. At least 1 driver mutation was identified in 96% of patient samples, with 2 or more driver mutations found in 86% of patient samples. This comprehensive analysis led to the identification of previously unidentified leukemia-associated genes, as well as complex co-mutation patterns within these patient samples, indicating a renewed need to evaluate the prognoses of prospective AML patients in light of a renewed genomic classification scheme. Eleven genomic subgroups were thus proposed in light of this comprehensive study.

Overall survival in these patient samples was correlated with the number of driver mutations, independent of age and cell count. Through a multivariate model designed to explore the relative contributions of genetic, clinical, and diagnostic variables to overall survival, genomic features were determined to be the most powerful predictor of overall patient survival.

This study thus demonstrated considerable differences in clinical presentation and overall survival among the identified genomic subgroups. This finding, together with the discovery that the prognostic effects of individual mutations were significantly altered by the presence or absence of other driving mutations, suggests the necessity of assessing a number of driving mutations present in AML patients to provide a more comprehensive individual patient prognosis.

One of the proposed genomic subgroups identified in the 1540-patient analysis relies on the presence of TP53, complex karyotype alterations, aneuploidies, or a combination thereof. Patients in this TP53/aneuploidy subgroup were characterized as older, with lower blasts, and displaying dismal responses to induction therapy. One such aneuploidy, trisomy 8 (occurring in 10-15% of AML patients), has been characterized as a "disease-modulating secondary event with underlying cryptic aberrations as it has been frequently reported in addition to known abnormalities contributing to clinical heterogeneity and modifying prognosis," and has been associated alternately as a poor or intermediate prognostic factor in AML patients. See Bakshi, S., et al. Trisomy 8 in leukemia: A GCRI experience. Indian J Hum Genet. 2012; 18:106-108.

Further, certain complex gene interactions, for instance, the three-way interaction between NPM1, DNMT3A, and FLT3-ITD, were found to amplify the deleterious effects of gene mutations existing in isolation. That is, the most deleterious effect of FLT3-ITD was most clinically relevant in patients with concomitant NPM1 and DNMT3A mutations; in the absence of either of these mutations, the deleterious effect of FLT3-ITD on patient prognosis was significantly less pronounced. Such an observation suggests that clinical associations with mutation hotspots/clusters, like FLT3, could be modulated by differences in co-mutated genes.

Consequently, the presence or absence of other driver lesions, including gene mutations, chromosomal aneuploidies, fusion genes, and complex karyotypes, has been demonstrated to provide a more comprehensive analysis of patient prognosis than the patient's status in one driver mutation alone. In light of this background, the need for the development of therapies capable of overcoming these particularly grim patient prognoses takes on a renewed importance.

The current invention seeks to overcome disadvantages of the prior art.

SUMMARY OF THE INVENTION

In one embodiment, the present invention includes a method for treating a FLT3 mutated proliferative disorder comprising: measuring expression of a mutated FLT3 or a constitutively active FLT3 mutant, and one or more genetic abnormalities in a sample obtained from a tumor sample obtained from the patient, wherein the presence of the one or more genetic abnormalities indicates that the patient has a poor prognosis; and administering to the patient a therapeutically effective amount of crenolanib or a pharmaceutically acceptable salt thereof, wherein the crenolanib increases a chance of survival of the patient having both the mutated FLT3 or the constitutively active FLT3 mutant and the one or more genetic abnormalities. In one aspect, the one or more genetic abnormalities are selected from at least one of a mutation in the RUNX1 or WT1 genes. In another aspect, the one or more genetic abnormalities is comprised of mutations in the FLT3-ITD, DNMT3A, and NPM1 genes. In another aspect, the one or more genetic abnormalities are at least one of trisomy 8 or trisomy 13. In another aspect, the proliferative disorder is selected from at least one of a leukemia, myeloma, myeloproliferative disease, myelodysplastic syndrome, idiopathic hypereosinophilic syndrome (HES), bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, and hematologic malignancy. In another aspect, the additional genetic abnormality is an aneuploidy, monosomy, trisomy, or polysomy. In another aspect, the one or more genetic abnormalities is a chromosomal aberration, a chromosomal deletion, a chromosomal duplication, a chromosomal translocation, a chromosomal inversion, a chromosomal insertion, a chromosomal ring, or an isochromosome. In another aspect, the one or more genetic abnormalities is a driver mutation in addition to the mutated FLT3. In another aspect, the driver mutation is selected from at least one of NPM1, DNMT3A, NRAS, KRAS, JAK2, PTPN11, TET2, IDH1, IDH2, WT1, RUNX1, CEBPA, ASXL1, BCOR, SF3B1, U2AF1, STAG2, SETBP1, ZRSR2, GRB7, SRSF2, MLL, NUP98, ETV6, TCL1A, TUSC3, BRP1, CD36, TYK2, or MUTYH. In another aspect, the therapeutically effective amount of crenolanib or the pharmaceutically acceptable salt thereof are from about 50 to 500 mg per day, 100 to 450 mg per day, 200 to 400 mg per day, 300 to 500 mg per day, 350 to 500 mg per day, or 400 to 500 mg per day; or the therapeutically effective amount of crenolanib or the pharmaceutically acceptable salt thereof is administered at least one of continuously, intermittently, systemically, or locally; or the therapeutically effective amount of crenolanib or the pharmaceutically acceptable salt thereof is administered orally, intravenously, or intraperitoneally. In another aspect, the crenolanib or the pharmaceutically acceptable salt thereof is crenolanib besylate, crenolanib phosphate, crenolanib lactate, crenolanib hydrochloride, crenolanib citrate, crenolanib acetate, crenolanib toluenesulphonate, and crenolanib succinate. In another aspect, the therapeutically effective amount of crenolanib or the pharmaceutically acceptable salt thereof is: administered up to three times or more a day for as long as the subject is in need of treatment for the proliferative disorder; or provided at least one of sequentially or concomitantly, with another pharmaceutical agent in a newly diagnosed proliferative disorder patient, to maintain remission of an existing patient, or in a relapsed/refractory proliferative disorder patient; or provided as a single agent or in combination with another pharmaceutical agent in a patient with a newly diagnosed proliferative disorder, to maintain remission, or in a relapsed/refractory proliferative disorder patient; or provided as a single agent or in combination with another pharmaceutical agent in a newly diagnosed proliferative disorder pediatric patient, to maintain remission, or in a relapsed/refractory proliferative disorder pediatric patient. In another aspect, the patient is relapsed/refractory to another tyrosine kinase inhibitor or chemotherapy.

In one embodiment, the present invention includes a method for treating a patient suffering from a proliferative disease comprising: identifying the patient in need of therapy for the proliferative disease and administering to the patient a therapeutically effective amount of Crenolanib or a salt thereof, wherein the proliferative disease is characterized by deregulated FLT3 receptor tyrosine kinase activity; wherein the proliferative disease is selected from at least one of a leukemia, myeloma, myeloproliferative disease, myelodysplastic syndrome, idiopathic hypereosinophilic syndrome (HES), bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, and hematologic malignancy; and wherein the patient comprises both a deregulated FLT3 receptor tyrosine kinase and one or more genetic abnormalities, wherein the presence of the one or more genetic abnormalities indicates that the patient has a poor prognosis and the Crenolanib or a salt thereof increases a chance of survival of the patient having both the mutated FLT3 and the one or more genetic abnormalities. In one aspect, the FLT3 mutation is selected from at least one of FLT3-ITD or FLT3-TKD. In another aspect, the one or more genetic abnormalities is an aneuploidy, monosomy, trisomy, or polysomy. In another aspect, the one or more genetic abnormalities is a chromosomal aberration, a chromosomal deletion, a chromosomal duplication, a chromosomal translocation, a chromosomal inversion, a chromosomal insertion, a chromosomal ring, or an isochromosome. In another aspect, the one or more genetic abnormalities include a driver mutation that is selected from at least one of NPM1, DNMT3A, NRAS, KRAS, JAK2, PTPN11, TET2, IDH1, IDH2, WT1, RUNX1, CEBPA, ASXL1, BCOR, SF3B1, U2AF1, STAG2, SETBP1, ZRSR2, GRB7, SRSF2, MLL, NUP98, ETV6, TCL1A, TUSC3, BRP1, CD36, TYK2, or MUTYH. In another aspect, the therapeutically effective amount of crenolanib or the pharmaceutically acceptable salt thereof is administered orally, intravenously, or intraperitoneally. In another aspect, the therapeutically effective amount of crenolanib or the pharmaceutically acceptable salt thereof is: at least one of Crenolanib Besylate, Crenolanib Phosphate, Crenolanib Lactate, Crenolanib Hydrochloride, Crenolanib Citrate, Crenolanib Acetate, Crenolanib Touluenesulphonate and Crenolanib Succinate; or is provided at least one of sequentially or concomitantly, with a chemotherapeutic agent in a newly diagnosed proliferative disease, to maintain remission, or a relapsed/refractory proliferative disease; or is provided as a single agent or in combination with a chemotherapeutic agent for treatment of pediatric patient with the proliferative disease; or is provided at least one of sequentially or concomitantly to at least one of post standard induction therapy, or high dose induction therapy, in newly diagnosed proliferative disease; or is provided as a single agent in treatment of patients with the proliferative disease that is either refractory to, or has relapsed after prior treatment with a chemotherapeutic agent. In another aspect, the patient is refractory to at least one other tyrosine kinase inhibitor or a chemotherapy.

In another embodiment, the present invention includes a method for treating a patient suffering from leukemia comprising: obtaining a sample from the patient suspected of having leukemia; determining from the patient sample that the patient has a deregulated FLT3 receptor or a constitutively active FLT3 receptor; further determining if the patient's leukemia is also characterized by an additional genetic abnormality; and administering to the patient in need of such treatment a therapeutically effective amount of crenolanib or a salt thereof, wherein the leukemia is characterized by the deregulated FLT3 receptor or the constitutively active FLT3 receptor and one or more genetic abnormalities causing a poor prognosis, wherein the crenolanib increases a chance of survival of the patient having both the deregulated FLT3 receptor or the constitutively active FLT3 receptor and the one or more genetic abnormalities. In one aspect, the leukemia is selected from: Hodgkin's disease; a myeloma; acute promyelocytic leukemia (APL); chronic lymphocytic leukemia (CLL); chronic myeloid leukemia (CML); chronic neutrophilic leukemia (CNL); acute undifferentiated leukemia (AUL); anaplastic large-cell lymphoma (ALCL); prolymphocytic leukemia (PML): juvenile myelomonocytic leukemia (JMML): adult T-cell ALL; acute myelogenous leukemia (AML), with trilineage myelodysplasia (AMLITMDS); mixed lineage leukemia (MLL); myelodysplastic syndromes (MDSs); myeloproliferative disorders (MPD); and multiple myeloma (MM). In another aspect, the FLT3 mutation is selected from at least one of FLT3-ITD or FLT3-TKD. In another aspect, the one or more genetic abnormalities is an aneuploidy, monosomy, trisomy, or polysomy. In another aspect, the one or more genetic abnormalities is a chromosomal aberration, a chromosomal deletion, a chromosomal duplication, a chromosomal translocation, a chromosomal inversion, a chromosomal insertion, a chromosomal ring, or an isochromosome. In another aspect, the one or more genetic abnormalities include a driver mutation that is selected from at least one of NPM1, DNMT3A, NRAS, KRAS, JAK2, PTPN11, TET2, IDH1, IDH2, WT1, RUNX1, CEBPA, ASXL1, BCOR, SF3B1, U2AF1, STAG2, SETBP1, ZRSR2, GRB7, SRSF2, MLL, NUP98, ETV6, TCL1A, TUSC3, BRP1, CD36, TYK2, or MUTYH.

In another embodiment, the present invention includes a method for specifically inhibiting a deregulated or constitutively active receptor tyrosine kinase, comprising: obtaining a sample; determining which receptor tyrosine kinases are deregulated or constitutively active; determining which of one or more genetic abnormalities are present; determining that the deregulated or constitutively active receptor tyrosine kinase and the one or more genetic abnormalities cause a poor prognosis; and administering to a mammal in need of such treatment a therapeutically effective amount of crenolanib or a salt thereof, wherein the crenolanib increases a chance of survival of the mammal having both the deregulated FLT3 receptor or the constitutively active FLT3 receptor and the one or more genetic abnormalities. In one aspect, the deregulated FLT3 receptor is selected from at least one of FLT3-ITD or FLT3-TKD. In another aspect, the one or more genetic abnormalities is an aneuploidy, monosomy, trisomy, or polysomy. In another aspect, the one or more genetic abnormalities is a chromosomal aberration, a chromosomal deletion, a chromosomal duplication, a chromosomal translocation, a chromosomal inversion, a chromosomal insertion, a chromosomal ring, or an isochromosome. In another aspect, the one or more genetic abnormalities include a driver mutation that is selected from at least one of NPM1, DNMT3A, NRAS, KRAS, JAK2, PTPN11, TET2, IDH1, IDH2, WT1, RUNX1, CEBPA, ASXL1, BCOR, SF3B1, U2AF1, STAG2, SETBP1, ZRSR2, GRB7, SRSF2, MLL, NUP98, ETV6, TCL1A, TUSC3, BRP1, CD36, TYK2, or MUTYH. In another aspect, the therapeutically effective amount of crenolanib or the salt thereof is provided: in an amount that decreases a patient's circulating peripheral blood blast count; or in an amount that decreases a patient's bone marrow blast count; or in an amount from about 50 to 500 mg per day, 100 to 450 mg per day, 200 to 400 mg per day, 300 to 500 mg per day, 350 to 500 mg per day, or 400 to 500 mg per day; or in an amount that is delivered at least one of continuously, intermittently, systemically, or locally. In another aspect, the therapeutically effective amount of crenolanib or the salt thereof is administered orally, intravenously, or intraperitoneally. In another aspect, the Crenolanib or the salt thereof is at least one of Crenolanib Besylate, Crenolanib Phosphate, Crenolanib Lactate, Crenolanib Hydrochloride, Crenolanib Citrate, Crenolanib Acetate, Crenolanib Touluenesulphonate and Crenolanib Succinate. In another aspect, the therapeutically effective amount of crenolanib or the salt thereof is at least one of: administered up to three times or more a day for as long as the subject is in need of treatment; or is provided at least one of sequentially or concomitantly, with another pharmaceutical agent in a newly diagnosed proliferative disease patient, to maintain remission, or in a relapsed/refractory proliferative disease patient; or the crenolanib or the salt thereof is provided as a single agent or in combination with another pharmaceutical agent in a newly diagnosed proliferative disease patient, to maintain remission, or in a relapsed/refractory proliferative disease patient; and/or the therapeutically effective amount of crenolanib or the salt thereof is provided as a single agent or in combination with another pharmaceutical agent in a newly diagnosed proliferative disease pediatric patient, to maintain remission, or in a relapsed/refractory proliferative disease pediatric patient. In another aspect, the patient is relapsed/refractory to a prior tyrosine kinase inhibitor.

In yet another embodiment, the present invention includes a method for treating a FLT3 mutated proliferative disorder in a patient, which comprises administering to the patient a therapeutically effective amount of crenolanib or a pharmaceutically acceptable salt thereof, wherein the patient has a QT interval (QTcF) >450 msec. In one aspect, the crenolanib is administered sequentially or concomitantly with another agent known to prolong the patient's QT interval. In another aspect, the agent is a 5-HT3 antagonist. In another aspect, the 5-HT3 antagonist is granisetron, odansetron, or dolasetron. In another aspect, the agent is one of itraconazole, ketoconazole, fluconazole, miconazole, posaconazole, omeprazole, esomeprazole, pantoprazole, voriconaprazole, metronidazole, haloperidol, pentamidine, amiodarone, ciprofloxacin, levofloxacin, moxifloxacin, azithromycin, and tacrolimus.

In yet another embodiment, the present invention includes a method for treating a FLT3 mutated proliferative disorder in a patient, which comprises administering to the patient a therapeutically effective amount of crenolanib or a pharmaceutically acceptable salt thereof, wherein the patient also has a heart condition and the crenolanib does not negatively impact the heart condition. In one aspect, the heart condition is one of hypertension, angina, acute myocardial infarction, subacute myocardial infarction, or arrhythmia.

In one embodiment, the present invention includes a method for treating a FLT3 mutated proliferative disorder further characterized by an additional genetic abnormality in a patient, which comprises administering to the patient a therapeutically effective amount of crenolanib or a pharmaceutically acceptable salt thereof.

Another embodiment of the present invention includes a method for treating a patient suffering from a proliferative disease comprising: identifying the patient in need of therapy for the proliferative disease and administering to the patient in need of such treatment a therapeutically effective amount of Crenolanib or a salt thereof, wherein the proliferative disease is characterized by deregulated FLT3 receptor tyrosine kinase activity, is selected from at least one of a leukemia, myeloma, myeloproliferative disease, myelodysplastic syndrome, idiopathic hypereosinophilic syndrome (HES), bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, and hematologic malignancy; and is further characterized by an additional genetic abnormality in the patient.

Yet another embodiment of the present invention includes a method for treating a patient suffering from leukemia comprising: obtaining a sample from the patient suspected of having leukemia; determining from the patient sample that the patient has a deregulated FLT3 receptor; further determining if the patient's leukemia is also characterized by an additional genetic abnormality; and administering to the patient in need of such treatment a therapeutically effective amount of crenolanib or a salt thereof, wherein the leukemia is characterized by deregulated FLT3 receptor tyrosine kinase activity and an additional genetic abnormality.

Yet another embodiment of the present invention includes a method for specifically inhibiting a deregulated receptor tyrosine kinase further characterized by an additional genetic abnormality, comprising: obtaining a patient sample; determining which receptor tyrosine kinases are deregulated; determining what additional genetic abnormalities are present; and administering to a mammal in need of such treatment a therapeutically effective amount of crenolanib or a salt thereof, wherein the deregulated receptor tyrosine kinase is a FLT3 receptor tyrosine kinase. In one aspect, the FLT3 receptor tyrosine kinase is defined further as a mutated FLT3 that is constitutively active. This summary of the invention does not necessarily describe all necessary features of the invention. This summary of the invention does not necessarily describe all necessary features of the invention.

BRIEF DESCRIPTION OF THE DRAWINGS

Not applicable.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention comprises the use of the compounds of the present invention to treat disorders related to FLT3 kinase activity or expression in a subject.

Crenolanib (4-Piperidinamine, 1-[2-[5-[(3-methyl-3-oxetanyl) methoxy]-1H-benzimidazol-1-yl]-8-quinolinyl]) and its pharmaceutically acceptable salts, are protein tyrosine kinase inhibitors selective for constitutively active FLT3 mutations, including FLT3 ITD and FLT3 TKD mutations. Unlike prior FLT3 inhibitors in the art, the besylate salt form of crenolanib has been shown to be remarkably effective in depleting circulating peripheral blood blast percentages and bone marrow blast percentages in heavily pretreated FLT3 mutant AML patients without significantly increasing patient QT prolongation. Crenolanib is currently being investigated for use in the treatment of patients with relapsed or refractory constitutively activated FLT3 mutated primary AML or AML secondary to myelodysplastic syndrome.

An analysis of Crenolanib's efficacy in patients presenting with concomitant FLT3 mutations, as well as other cytogenetic or molecular abnormalities, are also presently being developed through ongoing clinical trials.

Crenolanib safety and tolerability was evaluated between November 2003 and September 2006 in a phase I first-in-human dose-escalation single agent study in heavily pretreated patients with advanced solid tumors (Protocol A5301001; See N Lewis et al., J Clin Oncol. 2009; 27: p 5262-5269). Fifty-nine patients were enrolled and completed the study. Most treatment related adverse events were of grade 1 or 2 severity. There was no evidence of cumulative toxicity. In patients treated with lower drug dosages ranging from 60-200 mg once daily, the most common adverse events observed were grade 1 nausea and vomiting, which usually occurred approximately 45 minutes after dosing. There were no grade 3 or 4 toxicities in these patients. At higher doses 280 mg and 340 mg once daily, liver enzyme elevations were the most severe side effects. Liver enzyme levels returned to normal following the discontinuation of crenolanib. The present invention has demonstrated that the administration of 100 mg three times daily of crenolanib besylate to human patients diagnosed with constitutively activated FLT3 mutant relapsed or refractory AML does not always result in an elevation of liver enzymes. See Example two in Examples section of this patent application. It also demonstrates that when liver enzymes are elevated that liver enzyme levels can be decreased by discontinuing the drug for approximately 1 week and re-starting crenolanib at a reducing dosage of 80 mg three times daily.

No grade 2/3/4 QT prolongation was observed in any of the 59 patients treated in the phase I dose escalation safety study, despite crenolanib dose received. Similarly, there have been no significant differences in baseline QT prolongation and on-treatment QT prolongation in a currently ongoing pediatric glioma trial with twenty-four children being treated with the besylate form of crenolanib. Likewise, the present invention has shown no cases of QT prolongation following the administration of 100 mg of crenolanib besylate three times daily to human patients diagnosed with constitutively activated FLT3 mutant relapsed or refractory AML. Other FLT3 inhibitors known in the art have caused significant QTc prolongation leading to strict clinical study inclusion and exclusion criteria to prevent severe adverse events. For example, two separate quizartinib AML studies have revealed that the compound causes significant Q prolongation. In a 76 patient phase I single agent study evaluating the compound in both FLT3 wildtype and FLT ITD mutated relapsed and refractory AML identified QT prolongation as the dose limiting toxicity. See J Cortes et al. AC220, a potent, selective, second generation FLT3 receptor tyrosine kinase (RTK) inhibitor, in a first-in-human (FIH) phase I AML study. Blood (ASH Annual Meeting Abstracts) 2009 November Additionally, interim data from a phase II trial of quizartinib monotherapy in 62 patients with relapsed or refractory AML with FLT3 ITD activating mutations asymptomatic QT prolongation was one of the most common (>19%) drug related adverse events. QT prolongation of all grades occurred in 21 (34%) patients. More than half of the QT prolongation events recorded were grade 3 (18%). Reducing the starting dose of quizartinib by greater than 30% did not alleviate all cases of QT prolongation. See J Cortes et al. A phase II open-label, AC220 monotherapy efficacy study in patients with refractory/relapsed FLT3-ITD positive acute myeloid leukemia: updated interim results. Blood (ASH Annual Meeting Abstracts) 2011 December.

As used herein, the term "poor prognosis" refers to a decreased chance of survival (for example, decreased overall survival, relapse-free survival, or metastasis-free survival). For example, a poor prognosis has a decreased chance of survival includes a survival time of equal to or less than 60 months, such as 50 months, 40 months, 30 months, 20 months, 12 months, 6 months, or 3 months from time of diagnosis or first treatment or remission.

By contrast, a "good prognosis" refers to an increased chance of survival, for example increased overall survival, relapse-free survival, or metastasis-free survival. For example, a good prognosis has an increased chance of survival includes a survival time of at least 60 months from time of diagnosis, such as 60 months, 80 months, 100 months, 120 months, 150 months, or more from time of diagnosis or first treatment.

Detection of the mutated FLT3 and/or one or more genetic abnormalities can be performed using any suitable means known in the art. For example, detection of gene mutations can be accomplished by detecting nucleic acid molecules (such as DNA) using nucleic acid amplification methods (such as RT-PCR) or high-throughput sequencing (i.e. "next-generation sequencing"). Detection of chromosomal abnormalities can also be accomplished using karyotyping or in situ hybridization that detects structural and numerical alterations.

In mutated FLT3 tumors, the alteration in expression or presence of one or more genetic abnormalities, such as, e.g., chromosomal translocations, deletions, alternative gene splicing, mutations or deletions within coding or intron-exon boundary regions, can be lead to a measurable decrease in prognosis. In addition to a pre-existing FLT3 mutation, the additional genetic abnormalities disclosed herein significantly decrease the prognosis of the patient. A poor prognosis can refer to any negative clinical outcome, such as, but not limited to, a decrease in likelihood of survival (such as overall survival, relapse-free survival, or metastasis-free survival), a decrease in the time of survival (e.g., less than 5 years, or less than one year), presence of a malignant tumor, an increase in the severity of disease, a decrease in response to therapy, an increase in tumor recurrence, an increase in metastasis, or the like. In particular examples, a poor prognosis is a decreased chance of survival (for example, a survival time of equal to or less than 60 months, such as 50 months, 40 months, 30 months, 20 months, 12 months, 6 months or 3 months from time of diagnosis or first treatment).

In other embodiments of the method, the presence of the one or more genetic abnormalities (in addition to the FLT3 mutation) in the tumor sample relative to a control indicates a poor prognosis for the patient with the tumor. The method includes detecting the presence of one or more genetic abnormalities that lead to a poor prognosis that include, e.g., aneuploidy (e.g., monosomy, trisomy, or polysomy), a chromosomal aberration (e.g., a deletion, duplication, translocation, inversion, insertion, ring, or isochromosome), or the presence of a driver mutation, e.g., NPM1, DNMT3A, NRAS, KRAS, JAK2, PTPN11, TET2, IDH1, IDH2, WT1, RUNX1, CEBPA, ASXL1, BCOR, SF3B1, U2AF1, STAG2, SETBP1, ZRSR2, GRB7, SRSF2, MLL, NUP98, ETV6, TCL1A, TUSC3, BRP1, CD36, TYK2, or MUTYH.

As used herein, the phrases "mutations responsible for cancer" and "driver mutations" are used interchangeably to refer to mutations that are present in cancer tissues and which are capable of inducing carcinogenesis of cells. Generally, if a mutation is found in a cancer tissue in which no other known oncogene mutations exists (in other words, if a mutation exists in a mutually exclusive manner with known oncogene mutations), then the mutation can be determined to be a responsible mutation for cancer, and thus, a "driver mutation".

In one embodiment to this aspect, the present invention provides a method for reducing or inhibiting the kinase activity of FLT3 in a subject comprising the step of administering a compound of the present invention to the subject.

As used herein, the term "subject" or "patient" are used interchangeable to refer to an animal, such as a mammal or a human, who has been the object of medical treatment, observation or experiment.

In one embodiment to this aspect, the present invention provides a method for reducing or inhibiting the kinase activity of FLT3 in a subject comprising the step of administering a compound of the present invention to the subject.

The term "subject" refers to an animal, such as a mammal or a human, who has been the object of treatment, observation or experiment.

In other embodiments to this aspect, the present invention provides therapeutic methods for treating a subject with a cell proliferative disorder driven by aberrant kinase activity of mutant FLT3. In one example, the invention provides methods for treating a cell proliferative disorder related to mutant FLT3, comprising administration of a therapeutically effective amount of a pharmaceutical composition comprising a compound of the present invention in a subject. Administration of said therapeutic agent can occur upon manifestation of symptoms characteristic of the FLT3 driven cell proliferative disorder, such that a disease or disorder treated.

The term "therapeutically effective amount" as used herein, refers to an amount of active compound or pharmaceutical salt that elicits the biological or medicinal response in a subject that is being sought by a researcher, veterinarian, medical doctor or other clinician, which includes alleviation of the symptoms of the disease or disorder being treated.

Methods for determining therapeutically effective doses for pharmaceutical compositions comprising a compound of the present invention are known in the art.

As used herein, the term "composition" is intended to encompass a product comprising the specified ingredients in the specified amounts, as well as any product which results, directly or indirectly, from combinations of the specified ingredients in the specified amounts.

As used herein, the terms "disorder related to FLT3," or "disorders related to FLT3 receptor," or "disorders related to FLT3 receptor tyrosine kinase," or "FLT3 driven cell proliferative disorder" includes diseases associated with or implicating FLT3 activity, for example, mutations leading to constitutive activation of FLT3. Examples of "disorders related to FLT3" include disorders resulting from over stimulation of FLT3 due to mutations in FLT3, or disorders resulting from abnormally high amount of FLT3 activity due to abnormally high amount of mutations in FLT3. It is known that over-activity of FLT3 has been implicated in the pathogenesis of many diseases, including the following listed cell proliferative disorders, neoplastic disorders and cancers.

The term "cell proliferative disorders" refers to excess cell proliferation of one or more subset of cells in a multicellular organism resulting in harm (i.e. discomfort or decreased life expectancy) to the multicellular organism. Cell proliferative disorders can occur in different types of animals and humans. As used herein, "cell proliferative disorders" include neoplastic disorders.

The term "neoplastic disorder" as used herein, refers to a tumor resulting from abnormal or uncontrolled cellular growth. Examples of neoplastic disorders include, but are not limited to the following disorders, for instance: the myeloproliferative disorders, such as thrombocytopenia, essential thrombocytosis (ET), agnogenic myeloid metaplasia, myelofibrosis (MF), myelofibrosis with myeloid metaplasia (MMM), chronic idiopathic myelofibrosis (UIMF), and polycythemia vera (PV), the cytopenias, and pre-malignant myelodysplastic syndromes; cancers such as glioma cancers, lung cancers, breast cancers, colorectal cancers, prostate cancers, gastric cancers, esophageal cancers, colon cancers, pancreatic cancers, ovarian cancers, and hematological malignancies, including myelodysplasia, multiple myeloma, leukemias, and lymphomas. Examples of hematological malignancies include, for instance, leukemias, lymphomas, Hodgkin's disease, and myeloma. Also, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML, with trilineage myelodysplasia (AMLITMDS), mixed lineage leukemia (MLL), myelodysplastic syndromes (MDSs), myeloproliferative disorders (MPD), and multiple myeloma (MM).

The expression of mutated FLT3, constitutively active FLT3 mutant, and the one or more genetic abnormalities, can be determined using standard molecular biology techniques, including sequencing at the RNA or DNA level, protein expression, protein function, the presence or absence of the RNA, DNA, and/or protein, as will be known to those of skill in the art following the teachings of, e.g., standard techniques for sequencing (including Next Generation Sequencing (NGS)), cloning, RNA and DNA isolation, amplification and purification, detection and identification of chromosomal abnormalities, and various separation techniques are those known and commonly employed by those skilled in the art. A number of standard techniques are described in Sambrook et al. (1989) Molecular Cloning, Second Edition, Cold Spring Harbor Laboratory, Plainview, N.Y.; Maniatis et al. (1982) Molecular Cloning, Cold Spring Harbor Laboratory, Plainview, N.Y.; Wu (ed.) (1993) Meth. Enzymol. 218, Part I; Wu (ed.) (1979) Meth. Enzymol. 68; Wu et al. (eds.) (1983) Meth. Enzymol. 100 and 101; Grossman and Moldave (eds.) Meth. Enzymol. 65; Miller (ed.) (1972) Experiments in Molecular Genetics, Cold Spring Harbor Laboratory, Cold Spring Harbor, N.Y.; Old and Primrose (1981) Principles of Gene Manipulation, University of California Press, Berkeley; Schleif and Wensink (1982) Practical Methods in Molecular Biology; Glover (ed.) (1985) DNA Cloning Vol. I and II, IRL Press, Oxford, UK; Hames and Higgins (eds.) (1985) Nucleic Acid Hybridization, IRL Press, Oxford, UK; Setlow and Hollaender (1979) Genetic Engineering: Principles and Methods, Vols. 1-4, Plenum Press, New York; Fitchen, et al. (1993) Annu Rev. Microbiol. 47:739-764; Tolstoshev, et al. (1993) in Genomic Research in Molecular Medicine and Virology, Academic Press; and Ausubel et al. (1992) Current Protocols in Molecular Biology, Greene/Wiley, New York, N.Y. Abbreviations and nomenclature, where employed, are deemed standard in the field and commonly used in professional journals such as those cited herein. The above techniques can be used to detect genetic abnormalities such as aneuploidy, monosomy, trisomy, or polysomy; chromosomal aberrations such as one or more deletions, duplications, translocations, inversions, insertions, rings, or isochromosomes. Additional genetic abnormalities include driver mutations such as those selected from at least one of NPM1, DNMT3A, NRAS, KRAS, JAK2, PTPN11, TET2, IDH1, IDH2, WT1, RUNX1, CEBPA, ASXL1, BCOR, SF3B1, U2AF1, STAG2, SETBP1, ZRSR2, GRB7, SRSF2, MLL, NUP98, ETV6, TCL1A, TUSC3, BRP1, CD36, TYK2, or MUTYH, all of them human or animal, with the names available from Genecards.com, with current accession numbers, sequences, and probes to the same incorporated herein by reference.

In a further embodiment, the present invention can be combined with another therapy as a combination therapy for treating or inhibiting the onset of a cell proliferative disorder related to FLT3 in a subject. The combination therapy comprises the administration of a therapeutically effective amount of a compound of the present invention and one or more other anti-cell proliferation therapies including, but not limited to, chemotherapy and radiation therapy.

In an embodiment of the present invention, a compound of the present invention may be administered in combination with chemotherapy. Used herein, chemotherapy refers to a therapy involving a chemotherapeutic agent. A variety of chemotherapeutic agents may be used in combination with the present invention. By way of example only, taxane compounds, specifically docetaxel, is safely administered in combination with a compound of the present invention in a dosage of 75 mg per square meter (mg/m$^2$) of body surface area.

Chemotherapy is known to those skilled in the art. The appropriate dosage and scheme for chemotherapy will be similar to those already employed in clinical therapies wherein the chemotherapy is delivered in combination with other therapies or used alone.

In another embodiment of the present invention, compounds of the present invention may be administered in combination with radiation therapy. Used herein, "radiation therapy" refers to a therapy that comprises the exposure of a subject in need to radiation. Radiation therapy is known to those skilled in the art. The appropriate dosage and scheme for radiation therapy will be similar to those already employed in clinical therapies wherein the radiation therapy is delivered in combination with other therapies or used alone.

In another embodiment of the present invention, the compounds of the present invention may be administered in combination with a targeted therapy. As used herein, "targeted therapy" refers to a therapy targeting a particular class of proteins involved in tumor development or oncogenic signaling. For example, tyrosine kinase inhibitors against vascular endothelial growth factor have been used in treating cancers.

The present invention also includes methods that include the use of a second pharmaceutical agent in addition to compounds of the present invention, the two may be administered simultaneously or sequentially (in either order).

In one embodiment, the present invention therapeutically effective amounts of the compound having formula I:

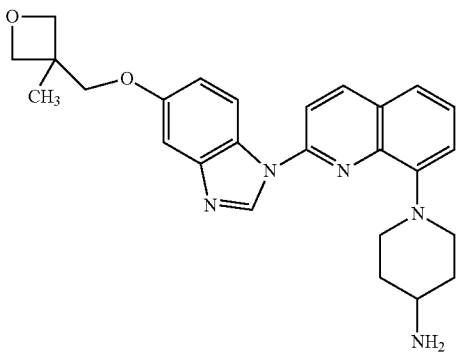 [SMILES: CC1(COc2ccc3c(c2)ncn3-c2ccc3cccc(N4CCC(N)CC4)c3n2)COC1]

or a pharmaceutically acceptable salt or solvate thereof, in a therapeutically or prophylactically effective amount against a proliferative disease is selected from at least one of a leukemia, myeloma, myeloproliferative disease, myelodysplastic syndrome, idiopathic hypereosinophilic syndrome (HES), bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, and hematologic malignancy. Pharmaceutically acceptable salts including hydrochloride, phosphate and lactate are prepared in a manner similar to the benzenesulfonate salt and are well known to those of moderate skill in the art.

Compounds of the present invention may be administered to a subject systemically, for example, orally, intravenously, subcutaneously, intramuscular, intradermal or parenterally. The compounds of the present invention can also be administered to a subject locally.

Compounds of the present invention may be formulated for slow-release or fast-release with the objective of maintaining contact of compounds of the present invention with targeted tissues for a desired range of time.

Compositions suitable for oral administration include solid forms, such as pills, tablets, caplets, capsules, granules, and powders, liquid forms, such as solutions, emulsions, and suspensions. Forms useful for parenteral administration include sterile solutions, emulsions and suspensions.

The daily dosage of the compounds of the present invention may be varied over a wide range from 50 to 500 mg per adult human per day. For oral administration, the compositions are preferably provided in the form of tablets containing 20 and 100 milligrams. The compounds of the present invention may be administered on a regimen up to three times or more per day. Preferably three times per day. Optimal doses to be administered may be determined by those skilled in the art, and will vary with the compound of the present invention used, the mode of administration, the time of administration, the strength of the preparation, the details of the disease condition. Factors associated with patient characteristics, such as age, weight, and diet will call for dosage adjustments.

Preparation of the compounds of the present invention. General synthetic methods which may be referred to for preparing the compounds of formula I are provided in U.S. Pat. No. 5,990,146 (issued Nov. 23, 1999) (Warner-Lambert Co.) and PCT published application numbers WO 99/16755 (published Apr. 8, 1999) (Merck & Co.) WO 01/40217 (published Jul. 7, 2001) (Pfizer, Inc.), US Patent Application Publication No. US 2005/0124599 (Pfizer, Inc.) and U.S. Pat. No. 7,183,414 (Pfizer, Inc.), relevant portions incorporated herein by reference.

Pharmaceutically acceptable salts such as hydrochloride, phosphate and lactate are prepared in a manner similar to the benzenesulfonate salt and are well known to those of moderate skill in the art. The following representative compounds of the present invention are for exemplary purposes only and are in no way meant to limit the invention, including Crenolanib as Crenolanib Besylate, Crenolanib Phosphate, Crenolanib Lactate, Crenolanib Hydrochloride, Crenolanib Citrate, Crenolanib Acetate, Crenolanib Toluenesulphonate and Crenolanib Succinate.

SUMMARY OF EXAMPLES

Example A: The leukemic blasts from a newly diagnosed patient harbored in addition to a FLT3-ITD mutation, mutations in the NPM1 and DNMT3A genes. The patient achieved reduction in bone marrow blasts to less than 5% following induction combination chemotherapy followed by sequential administration of crenolanib besylate.

Example B: The leukemic blasts from a newly diagnosed patient harbored in addition to a FLT3-ITD mutation, a mutation in the RUNX1 gene. The patient achieved reduction in bone marrow blasts to less than 5% following induction combination chemotherapy followed by sequential administration of crenolanib besylate and was bridged to an allogeneic hematopoietic stem cell transplantation (HSCT).

Example C: The leukemic blasts from a newly diagnosed patient harbored in addition to a FLT3-ITD mutation, a mutation in the RUNX1 gene and an abnormal karyotype containing trisomy 8 and trisomy 13. The patient achieved reduction in bone marrow blasts to less than 5% following induction combination chemotherapy followed by sequential administration of crenolanib besylate and was bridged to an allogeneic hematopoietic stem cell transplantation (HSCT).

Example D: The leukemic blasts from a relapsed/refractory patient harbored in addition to a FLT3-ITD mutation, an abnormal karyotype containing trisomy 8 and a (6;9) translocation. The patient achieved reduction in bone marrow blasts to less than 5% following salvage combination chemotherapy followed by sequential administration of crenolanib besylate.

Example E: The leukemic blasts from a newly diagnosed patient harbored in addition to a FLT3-ITD mutation, a mutation in the WT1 gene. The patient achieved reduction in bone marrow blasts to less than 5% following induction combination chemotherapy followed by sequential administration of crenolanib besylate and was bridged to an allogeneic hematopoietic stem cell transplantation (HSCT).

Example F: The leukemic blasts from a relapsed/refractory patient with prior TKI failure harbored, in addition to a FLT3-ITD mutation, a mutation in the WT1 gene. The patient achieved reduction in bone marrow blasts to less than 5% following crenolanib besylate monotherapy.

Example G: The leukemic blasts from a relapsed/refractory patient with prior TKI failure harbored, in addition to a FLT3-ITD mutation, an abnormal complex karyotype. The patient achieved reduction in bone marrow blasts to less than 5% following induction combination chemotherapy followed by sequential administration of crenolanib besylate and was bridged to an allogeneic hematopoietic stem cell transplantation (HSCT).

Example H: The leukemic blasts from a relapsed/refractory patient with prior TKI failure harbored in addition to a FLT3-ITD mutation, mutations in the NPM1, DNMT3A, and WT1 genes and an abnormal complex karyotype. The patient achieved reduction in bone marrow blasts to less than 10% following crenolanib besylate monotherapy.

Example A: Effect of Crenolanib Besylate Therapy in a Newly Diagnosed AML Patient with FLT3-ITD, NPM1, and DNMT3A Mutations with Normal Karyotype: Achievement of reduction in bone marrow blasts to less than 5% with hematologic recovery.

A 54-year-old female was diagnosed with AML positive for both FLT3-ITD and FLT3-TKD mutations. The patient's leukemic blasts also had mutations in the NPM1 and DNMT3A genes. As the FLT3-ITD, NPM1, and DNMT3A mutations are characterized as independent driver mutations, and are together associated with a particularly poor prognosis, the patient's presentation of these triple mutations placed her in a significantly high-risk group for AML patients, associated with poor response rates, increased cumulative incidence of relapse, and shortened survival. Half of patients with these mutations are expected to die within 1 year of diagnosis. See Papaemmanuil, E., "Genomic Classification and Prognosis in Acute Myeloid Leukemia," New England J. Med. Vol. 374, No. 23, pp. 2209-2221 (9 Jun. 2016).

At diagnosis, the patient was found to have 63% bone marrow blasts. Following diagnosis, the patient was provided with oral crenolanib besylate on a clinical trial newly diagnosed AML patients (NCT02283177). The patient was initially treated with induction chemotherapy, comprised of seven days of cytarabine and three days of daunorubicin; the patient began therapy with 100 mg of crenolanib besylate three times daily on day 10.

A bone marrow biopsy taken on day 35 of the clinical trial revealed the patient's bone marrow blasts had reduced to less than 5%, classified as a complete remission. The patient remains alive and free of disease more than one year after start of therapy.

Table A below illustrates the ability of crenolanib to clear and maintain clearance of malignant leukemia in the bone marrow of Example A, a newly diagnosed AML patient with FLT3-ITD, NPM1, and DNMT3A mutations with normal karyotype after treatment with chemotherapy and crenolanib besylate.

| Days on Clinical Trial | Bone Marrow Blast (%) |
|---|---|
| 0 | 63% |
| 35 | <5% |
| 238 | <5% |
| 294 | <5% |
| 406 | <5% |

Example B: Effect of Crenolanib Besylate Therapy in a Newly Diagnosed AML Patient with FLT3-ITD and RUNX1 Mutations with Normal Karyotype: Achievement of reduction in bone marrow blasts to less than 5% with hematologic recovery.

A 23-year-old female was diagnosed with AML positive for FLT3-ITD, RUNX1, and DNMT3A mutations. FLT3-ITD and RUNX1 mutations both independently categorize her as a high-risk AML patient, which is associated with poor response rate, increased cumulative incidence of relapse, and shortened survival.

At diagnosis, the patient was found to have 70% bone marrow blasts. Following diagnosis, the patient was provided with oral crenolanib besylate on a clinical trial newly diagnosed AML patients (NCT02283177). The patient was initially treated with induction chemotherapy, comprised of seven days of cytarabine and three days of daunorubicin; the patient began therapy with 100 mg of crenolanib besylate three times daily on day 9.

A bone marrow biopsy taken on day 36 of the clinical trial revealed the patient's bone marrow blasts had reduced to less than 5%, classified as a complete remission. The patient remains alive and free of disease more than 600 days after start of therapy. Less than 15% of patients with RUNX1 mutations treated with standard therapy would be expected to survive without disease for more than 600 days. See Mendler, J RUNX1 Mutations Are Associated With Poor Outcome in Younger and Older Patients With Cytogenetically Normal Acute Myeloid Leukemia and With Distinct Gene and MicroRNA Expression Signatures. J Clin. Oncol. 2012; 30:3109-3118.

Table B below illustrates the ability of crenolanib to clear and maintain clearance of malignant leukemia in the bone marrow of Example B, a newly diagnosed AML patient with FLT3-ITD and RUNX1 mutations with normal karyotype after treatment with chemotherapy and crenolanib besylate.

| Days on Clinical Trial | Bone Marrow Blast (%) |
|---|---|
| 0 | 70% |
| 36 | <5% |
| 96 | <5% |
| 120 | <5% |

* No additional bone marrow biopsies were performed on study after day 120, as the patient remained in remission.

Example C: Effect of Crenolanib Besylate Therapy in a Newly Diagnosed AML Patient with FLT3-ITD and RUNX1 Mutations, Trisomy 8, and Trisomy 13: Achievement of reduction in bone marrow blasts to less than 5% with hematologic recovery.

A 34-year-old female was diagnosed with AML, positive for FLT3-ITD and RUNX1 mutations. These mutations independently categorize her as a high-risk AML patient, which is associated with poor response rate, increased cumulative incidence of relapse, and shortened survival.

The patient was further shown to exhibit an abnormal karyotype, characterized by the appearance of trisomy 8 and trisomy 13. Trisomy 8 has been characterized as an independent driver mutation separate and apart from other driver mutations characteristic of AML (such as the patient's FLT3 mutational status) and has itself been independently associated with a poor prognosis. Trisomy 13 is also an independent, poor prognostic factor and has been strongly associated with RUNX1 mutations. See Dicker, F., et al. Trisomy 13 is strongly associated with AML1/RUNX1 mutations and increased FLT3 expression in acute myeloid leukemia. Blood. 2007; 110:1308-1316. The patient's presentation of these combined mutational and cytogenetic characteristics placed her in a higher risk group than the FLT3-ITD mutation alone.

At diagnosis, the patient was found to have 81% bone marrow blasts. Following diagnosis, the patient was provided with oral crenolanib besylate on a clinical trial newly diagnosed AML patients (NCT02283177). The patient was initially treated with induction chemotherapy, comprised of seven days of cytarabine and three days of daunorubicin; the patient began therapy with 100 mg of crenolanib besylate three times daily on day 9.

A bone marrow biopsy taken on day 36 of the clinical trial revealed the patient's bone marrow blasts had reduced to less than 5%, classified as a complete remission, and the presence of FLT3-ITD and RUNX1 mutations were no longer detectable. A karyotype analysis further revealed that the patient now exhibited a normal karyotype, with no clonal abnormalities detected including neither trisomy 8 nor trisomy 13, as had been detected at baseline. The patient remains alive and free of disease for more than 500 days after start of therapy. Less than 10% of patients with these mutations treated with standard therapy would be expected to survive without disease for more than 500 days. See Herold, T., Isolated trisomy 13 defines a homogeneous AML subgroup with high frequency of mutations in spliceosome genes and poor prognosis. Blood. 2014; 124:1304-1311.

Table C below illustrates the ability of crenolanib to clear and maintain clearance of malignant leukemia in the bone marrow of Example C, a newly diagnosed AML patient with FLT3-ITD and RUNX1 mutations and trisomy 8 and trisomy 13 after treatment with chemotherapy and crenolanib besylate.

| Days on Clinical Trial | Bone Marrow Blast (%) |
| --- | --- |
| 0 | 81% |
| 36 | <5% |
| 74 | <5% |
| 144 | <5% |

* No additional bone marrow biopsies were performed on study after day 144, as the patient remained in remission.

Example D: Effect of Crenolanib Besylate Therapy in a Relapsed/Refractory AML Patient with a FLT3-ITD Mutation, Trisomy 8, and (6;9) Translocation: Achievement of reduction in bone marrow blasts to less than 5% with hematologic recovery.

A 75-year-old male was diagnosed with AML positive for a FLT3-ITD mutation and harbored a (6;9) translocation, both of which independently categorized him as a high-risk AML patient, which is associated with poor response rate, increased cumulative incidence of relapse, and shortened survival. See Papaemmanuil, E., et al. Genomic Classification and Prognosis in Acute Myeloid Leukemia. N Engl J Med. 2016; 374:2209-2221.

Following his diagnosis, the patient was initially treated with induction chemotherapy. Approximately seven months later the patient had relapsed with a bone marrow blast percentage of 39%.

Further genetic analysis showed that the patient had acquired a trisomy 8 chromosomal abnormality in addition to the FLT3-ITD and (6;9) translocation that were present upon initial diagnosis. As trisomy 8 has been also been characterized as an independent driver mutation separate and apart from other driver mutations characteristic of AML (such as the patient's FLT3 mutational status and (6;9) translocation) and has itself been associated with a poor prognosis, the patient's presentation of these three characteristics placed him in a significantly higher risk group.

At the time of relapse, the patient was provided with oral crenolanib besylate on a clinical trial for relapsed or refractory AML patients (NCT02626338). The patient was initially treated with salvage chemotherapy, comprised of six days of cytarabine and three days of mitoxantrone; the patient began therapy with 100 mg of crenolanib besylate three times daily on day 8.

A bone marrow biopsy taken on day 34 of the clinical trial revealed the patient's bone marrow blasts had reduced to less than 5%, classified as a complete remission. Further analysis revealed that the patient now exhibited a normal male karyotype. The patient remained in remission for more than 400 days. Less than 10% of relapsed patients with these mutations treated with standard therapy would be expected to survive for more than 400 days. See Levis, M., et al. Results from a randomized trial of salvage chemotherapy followed by lestaurtinib for patients with FLT3 mutant AML in first relapse. Blood. 2011; 117:3294-3301.

Table D below illustrates the ability of crenolanib to clear and maintain clearance malignant leukemia in the bone marrow of Example D, a relapsed/refractory AML patient with a FLT3-ITD mutation, trisomy 8, and (6;9) translocation after treatment with salvage chemotherapy and crenolanib besylate.

| Days on Clinical Trial | Bone Marrow Blast (%) |
| --- | --- |
| 0 | 39% |
| 34 | <5% |
| 115 | <5% |

* No additional bone marrow biopsies were performed on study after day 115, as the patient remained in remission.

Example E: Effect of Crenolanib Besylate Therapy in a Newly Diagnosed AML Patient with FLT3-ITD and WT1 Mutations with Normal Karyotype: Achievement of reduction in bone marrow blasts to less than 5% with hematologic recovery.

A 22-year-old female was diagnosed with AML positive for FLT3-ITD, WT1 and NPM1 mutations. FLT3-ITD and WT1 mutations both independently categorize her as a high-risk AML patient, which is associated with poor response rate, increased cumulative incidence of relapse, and shortened survival.

At diagnosis, the patient was found to have 65% bone marrow blasts. Following diagnosis, the patient was provided with oral crenolanib besylate on a clinical trial newly diagnosed AML patients (NCT02283177). The patient was initially treated with induction chemotherapy, comprised of seven days of cytarabine and three days of idarubicin; the patient began therapy with 100 mg of crenolanib besylate three times daily on day 12.

A bone marrow biopsy taken on day 34 of the clinical trial revealed the patient's bone marrow blasts had reduced to less than 5%, classified as a complete remission. The patient remains alive and free of disease more than 700 days after start of therapy. Less than 15% of patients with WT1 mutations treated with standard therapy would be expected to survive without disease for more than 700 days. See Paschka, P., et al. Wilms' Tumor 1 Gene Mutations Independently Predict Poor Outcome in Adults With Cytogenetically Normal Acute Myeloid Leukemia: A Cancer and Leukemia Group B Study. J Clin Oncol. 2008; 26:4595-4602.

Table E below illustrates the ability of crenolanib to clear and maintain clearance of malignant leukemia in the bone marrow of Example E, a newly diagnosed AML patient with FLT3-ITD and WT1 mutations with normal karyotype after treatment with chemotherapy and crenolanib besylate.

| Days on Clinical Trial | Bone Marrow Blast (%) |
|---|---|
| 0 | 65% |
| 34 | <5% |
| 82 | <5% |
| 196 | <5% |

Example F: Effect of Crenolanib Besylate Therapy in a Relapsed/Refractory AML Patient with FLT3-ITD and WT1 Mutations with Normal Karyotype: Achievement of reduction in bone marrow blasts to less than 5% with hematologic recovery.

A 72-year-old female was diagnosed with AML and initially treated with induction chemotherapy. Approximately four months later, the patient relapsed and was treated with multiple salvage therapies, including the multikinase inhibitor midostaurin due to the presence of a FLT3-ITD mutation. Six weeks following an allogenic stem cell transplant, the patient relapsed again. The patient's history of multiple relapses and prior kinase inhibitor treatment placed this patient in a high-risk group.

Further analysis showed that the patient had mutations in the FLT3-ITD gene as well as the WT1 gene. As WT1 mutations have been associated with poor prognosis and treatment failure, the co-occurrence of FLT3-ITD and WT1 mutations placed the patient in an even higher risk group. See Paschka, P., et al. Wilms' Tumor 1 Gene Mutations Independently Predict Poor Outcome in Adults With Cytogenetically Normal Acute Myeloid Leukemia: A Cancer and Leukemia Group B Study. J Clin Oncol. 2008; 26:4595-4602.

At the time of relapse following allogeneic stem cell transplant, the patient was provided with oral crenolanib besylate on a clinical trial for relapsed or refractory AML patients (NCT01657682). The patient began therapy with 200 mg/m$^2$ per day of crenolanib besylate.

A bone marrow biopsy taken on day 54 of the clinical trial revealed the patient's bone marrow blasts had reduced to less than 5%, classified as a complete remission.

Table F below illustrates the ability of crenolanib to clear malignant leukemia in the bone marrow of Example F, a relapsed/refractory AML patient with FLT3-ITD and WT1 mutations with prior TKI failure.

| Days on Clinical Trial | Bone Marrow Blast (%) |
|---|---|
| 0 | 15% |
| 29 | 12% |
| 54 | <5% |

Example G: Effect of Crenolanib Besylate Therapy in a Relapsed/Refractory AML Patient with a FLT3-ITD Mutation and Complex Karyotype: Achievement of reduction in bone marrow blasts to less than 5% with hematologic recovery.

A 43-year-old female was diagnosed with AML positive for a FLT3-ITD mutation. The patient did not respond to initial therapy, which included induction chemotherapy and sorafenib (a tyrosine kinase inhibitor). The patient had 19% bone marrow blasts at the end of initial therapy, which indicated she was still positive for a FLT3-ITD mutation and also exhibited an abnormal karyotype consisting of monosomy 15, trisomy 21, trisomy 11, dicentric centromeres, and derivative chromosomes. A FLT3-ITD mutation and a complex karyotype both independently categorized her as a high-risk AML patient, which is associated with poor response rate, increased cumulative incidence of relapse, and shortened survival. See Papaemmanuil, E., "Genomic Classification and Prognosis in Acute Myeloid Leukemia," New England J. Med. Vol. 374, No. 23, pp. 2209-2221 (9 Jun. 2016).

The patient was then provided with oral crenolanib besylate on a clinical trial for relapsed or refractory AML patients (NCT02400281). The patient was initially treated with salvage chemotherapy, comprised of four days of cytarabine and three days of idarubicin; the patient began therapy with 100 mg of crenolanib besylate three times daily on day 5.

A bone marrow biopsy taken on day 20 of the clinical trial revealed the patient's bone marrow blasts had reduced to less than 5%, classified as a complete remission. The patient remained in remission for over 200 days. Less than 20% of relapsed/refractory patients with these mutations treated with standard therapy would be expected to achieve a complete remission. See Levis, M., et al. Results from a randomized trial of salvage chemotherapy followed by lestaurtinib for patients with FLT3 mutant AML in first relapse. Blood. 2011; 117:3294-3301.

Table G below illustrates the ability of crenolanib to clear malignant leukemia in the bone marrow of Example G, a relapsed/refractory AML patient with FLT3-ITD mutation and complex karyotype with prior TKI failure after treatment with salvage chemotherapy and crenolanib besylate.

| Days on Clinical Trial | Bone Marrow Blast (%) |
|---|---|
| 0 | 19% |
| 20 | <5% |

Example H: Effect of Crenolanib Besylate Therapy in a Relapsed/Refractory AML Patient with a FLT3-ITD mutation and Complex Karyotype: Achievement of reduction in bone marrow blasts to less than 10% with hematologic recovery.

A 48-year-old female was diagnosed with AML positive for a FLT3-ITD mutation and normal female karyotype and initially treated with induction chemotherapy. Approximately seven months later, the patient relapsed and received multiple salvage therapies including chemotherapy and the tyrosine kinase inhibitor, sorafanib. The patient did not respond to these therapies and had 46% bone marrow blasts following treatment, which blasts were positive for FLT3-ITD, FLT3-TKD, NPM1, DNMT3A, and WT1 mutations. Presence of concurrent FLT3-ITD, NPM1, and DNMT3A mutations and a WT1 mutation both placed the patient in a high-risk group. The patient was further shown to exhibit an abnormal complex karyotype characterized by translocations (1;6), (4;19), and (10;15). As complex karyotype has been characterized as an independent driver mutation separate and apart from other driver mutations characteristic of AML (such as the patient's FLT3 mutational status) and has itself been associated with a poor prognosis, the patient's presentation of these three sets of characteristics placed her in a significantly higher risk group.

The patient was then provided with oral crenolanib besylate of single-agent crenolanib in relapsed or refractory AML patients (NCT01657682). The patient began therapy with 200 mg/m$^2$ per day of crenolanib besylate.

A bone marrow biopsy taken on day 29 of the clinical trial revealed the patient's bone marrow blasts had reduced to 7%, classified as a partial remission.

Table H below illustrates the ability of crenolanib to significantly reduce malignant leukemia in the bone marrow of Example H, a relapsed/refractory AML patient with FLT3-ITD and WT1 mutations and complex karyotype with prior TKI failure.

| Days on Clinical Trial | Bone Marrow Blast (%) |
|---|---|
| 0 | 46% |
| 29 | 7% |

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

DREXLER, et al. "Expression of FLT3 receptor and response to FLT3 ligand by leukemic cells" Leukemia. Apr. 10, 1996; 10:588-599 (ABSTRACT ONLY)

GILLILAND, et al. "The roles of FLT3 in hematopoiesis and leukemia." Blood. Sep. 1, 2002; 100: 1532-1542

STIREWALT, et al. "The role of FLT3 in haematopoietic malignancies" Nature Reviews Cancer. 2003; 3:650-665

NAKAO, et al. ABSTRACT ONLY: "Internal tandem duplication of the FLT3 gene found in acute myeloid leukemia." Leukemia. 1996; 10:1911-1918

KIYOI, et al. "Internal tandem duplication of the FLT3 gene is a novel modality of elongation mutation which causes constitutive activation of the product" Leukemia. 1998; 12:1333-1337

KOTTARIDIS, et al. "The presence of a FLT3 internal tandem duplication in patients with acute myeloid leukemia (AML) adds important prognostic information to cytogenetic risk group and response to the first cycle of chemotherapy: analysis of 854 patients from the United Kingdom Medical Research Counsel AML 10 and 12 trials" Blood. Sep. 15, 2001; 98: 1742-1759

YAMAMOTO, et al. "Activating mutation of D835 within the activation loop of FLT3 in human hematologic malignancies" Blood. 2001; 97"2434-2439

THIEDE, et al. "Analysis of FLT3-activating mutations in 979 patients with acute myelogenous leukemia: association with FAB subtypes and identification of subgroups with poor prognosis" Blood. 2002; 99:4326-4335

BAINS, et al. "FLT3 and NPM1 mutations in myelodysplastic syndromes: Frequency and potential value for predicting progression to acute myeloid leukemia" American Journal of Clinical Pathology. January 2011; 135: 62-69

BHAMIDPATI, et al. "FLT3 mutations in myelodysplastic syndromes (MDS) and chronic myelomonocytic leukemia (CMML). 2012. Journal of Clinical Oncology. Suppl; abstract 6597

KIYOI, et al. "Internal tandem duplication of FLT3 associated with leukocytosis in acute promyelocytic leukemia" Leukemia Study Group of the Ministry of Health and Welfare (Kohseisho). Leukemia. 1997; 11: 1447-1452

SCHNITTGER, et al. "Analysis of FLT3 length mutations in 1003 patients with acute myeloid leukemia: correlation to cytogenetics, FAB subtype, and prognosis in the AMLCG study and usefulness as a marker for the detection of minimal residual disease" Blood. 2002; 100: 59-66

ABU-DUHIER, et al. "FLT3 internal tandem duplication mutations in adult acute myeloid leukemia define a high-risk group" British Journal of Hematology. Jun. 7, 2000; 111: 190-195

KIYOI et al. "Prognostic implication of FLT3 and N-RAS gene mutations in acute myeloid leukemia" Blood. May 1, 1999; 93:3074-3080

BACHER, et al. "Prognostic relevance of FLT3-TKD mutations in AML: the combination matters—an analysis of 3082 patients" Blood. Mar. 1, 2008; 111:2527-2537

KINDLER, et al. "FLT3 as a therapeutic target in AML: still challenging after all these years" Blood. Dec. 9, 2010; 116:5089-102

LEVIS, et al. "A FLT3 tyrosine kinase inhibitor is selectively cytotoxic to acute myeloid leukemia blasts harboring FLT3 internal tandem duplication mutations" Blood. Aug. 1, 2001; 98(3): 885-887

SMITH, et al. Single agent CEP-701, a novel FLT3 inhibitor, shows biologic and clinical activity in patients with relapsed or refractory acute myeloid leukemia Blood, May 2004; 103: 3669-3676

GRISWOLD, et al. "Effects of MLN518, a dual FLT3 and KIT inhibitor, on normal and malignant hematopoiesis" Blood. November 2004; 104 (9): 2912-2918

YEE, et al., SU5416 and SU5614 inhibit kinase activity of wild-type and mutant FLT3 receptor tyrosine kinase. Blood, October 2002; 100(8): 2941-2949

O'Farrell et al., SU11248 is a novel FLT3 tyrosine kinase inhibitor with potent activity in vitro and in vivo. Blood, May 2003; 101(9): 3597-3605

Murata, K. et al., Selective cytotoxic mechanism of GTP-14564, a novel tyrosine kinase inhibitor in leukemia cells expressing a constitutively active Fms-like tyrosine kinase 3 (FLT3). J Biol Chem. Aug. 29, 2003; 278 (35): 32892-32898 [Epub 2003 Jun. 18]

Stone, R. M et al., PKC-412 FLT3 inhibitor therapy in AML: results of a phase II trials. Ann. Hematol. 2004; 83 Suppl 1:S89-90

CHESON, et al. "Revised Recommendations of the International Working Group for Diagnosis, Standardization of Response Criteria, Treatment Outcomes, and Reporting Standards for Therapeutic Trials in Acute Myeloid Leukemia" J Clin Oncol. Dec. 15, 2003; 21: 4642-4649

LEVIS, et al. "Small Molecule FLT3 Tyrosine Kinase Inhibitors" Current Pharmaceutical Design. 2004, 10, 1183-1193

BORTHAKUR, et al. "Phase I study of sorafenib in patients with refractory or relapsed acute leukemias." Haematologica. January 2011; 96: 62-8. Epub Oct. 15, 2010

Small D. FLT3 mutations: biology and treatment. Hematology Am Soc Hematol Educ Program. 2006: 178-84

AMIN, et al. "Having a higher blast percentage in circulation than bone marrow; clinical implications in myelodysplastic syndrome and acute lymphoid and myeloid leukemias" Leukemia. Jul. 28, 2005: 19: 1567-72

VANDERWALDE, A., "Genetics of Acute Myeloid Leukemia," available at http://emedicine.medscape.com/article/1936033-overview (last updated 1 Apr. 2016)

PAPAEMMANUIL, E., "Genomic Classification and Prognosis in Acute Myeloid Leukemia," New England J. Med. Vol. 374, No. 23, pp. 2209-2221 (9 Jun. 2016)

DÖHNER, H., et al. "Diagnosis and management of AML in adults: 2017 ELN recommendations from an international expert panel," Blood. Vol. 129, No. 3, pp. 424-447 (28 Nov. 2016).

BAKSHI, S., et al. "Trisomy 8 in leukemia: A GCRI experience," Indian J Hum Genet. 2012; 18:106-108.

LEWIS, et al. "Phase I study of the safety, tolerability, and pharmacokinetics of oral CP-868-596, a highly specific platelet-derived growth factor receptor tyrosine kinase inhibitor in patients with advanced cancers" J Clin Oncol. Nov. 1, 2009; 27(31), 5262-5269

CORTES, et al. "AC220, a potent, selective, second generation FLT3 receptor tyrosine kinase (RTK) inhibitor, in a first-in-human (FIH) phase I AML study" Blood (ASH Annual Meeting Abstracts) 2009 November CORTES, et al. "A phase II open-label, AC220 monotherapy efficacy study in patients with refractory/relapsed FLT3-ITD positive acute myeloid leukemia: updated interim results" Blood (ASH Annual Meeting Abstracts) 2011 December MENDLER, J "RUNX1 Mutations Are Associated With Poor Outcome in Younger and Older Patients With Cytogenetically Normal Acute Myeloid Leukemia and With Distinct Gene and MicroRNA Expression Signatures," J. Clin. Oncol. Vol. 30, No. 25, pp. 3109-3118 (2 Jul. 2012)

DICKER, F., et al. "Trisomy 13 is strongly associated with AML1/RUNX1 mutations and increased FLT3 expression in acute myeloid leukemia," Blood. 2007; 110:1308-1316.

HEROLD, T., et al. "Isolated trisomy 13 defines a homogeneous AML subgroup with high frequency of mutations in spliceosome genes and poor prognosis," Blood. 2014; 124:1304-1311.

LEVIS, M., et al. "Results from a randomized trial of salvage chemotherapy followed by lestaurtinib for patients with FLT3 mutant AML in first relapse," Blood. 2011; 117:3294-3301.

PASCHKA, P., et al. "Wilms' Tumor 1 Gene Mutations Independently Predict Poor Outcome in Adults With Cytogenetically Normal Acute Myeloid Leukemia: A Cancer and Leukemia Group B Study," J Clin Oncol. 2008; 26:4595-4602.

What is claimed is:

1. A method for treating human patient suffering from leukemia with crenolanib, where the leukemia is characterized by one or more deregulated FLT3 receptors, or one or more constitutively active FLT3 receptors, and one or more driver mutations in a DNMT3A gene, the method comprising:
   first, obtaining a biological sample from a human patient's leukemia;
   then assaying the biological sample for expression of the deregulated FLT3 receptor or the constitutively active FLT3 receptor, and expression of one or more driver mutations in the DNMT3A gene;
   then determining that the human patient has a poor prognosis of leukemia based on the detection of the deregulated FLT3 receptor or the constitutively active FLT3 receptor, and the presence of the one or more driver mutations in the DNMT3A gene; and
   then administering to the patient a therapeutically effective amount of crenolanib or a pharmaceutically acceptable salt thereof, thereby treating the leukemia which has both the deregulated FLT3 receptor or the constitutively active FLT3 receptor and the one or more driver mutations in the DNMT3A gene.

2. The method of claim 1, wherein the therapeutically effective amount of crenolanib or the pharmaceutically acceptable salt thereof are from about 50 to 500 mg per day, 100 to 450 mg per day, 200 to 400 mg per day, 300 to 500 mg per day, 350 to 500 mg per day, or 400 to 500 mg per day; or
   the therapeutically effective amount of crenolanib or the pharmaceutically acceptable salt thereof is administered orally, intravenously, or intraperitoneally.

3. The method of claim 1, wherein the crenolanib or the pharmaceutically acceptable salt thereof is crenolanib besylate, crenolanib phosphate, crenolanib lactate, crenolanib hydrochloride, crenolanib citrate, crenolanib acetate, crenolanib toluenesulphonate, or crenolanib succinate.

4. The method of claim 1, wherein the therapeutically effective amount of crenolanib or the pharmaceutically acceptable salt thereof is:
   administered up to three times or more a day for as long as the subject is in need of treatment for the leukemia; or
   provided at least one of sequentially or concomitantly, with another pharmaceutical agent in a newly diagnosed leukemia patient, to maintain remission of an existing patient, or in a relapsed/refractory leukemia patient; or
   provided as a single agent or in combination with another pharmaceutical agent in a patient with a newly diagnosed leukemia, to maintain remission, or in a relapsed/refractory leukemia patient; or
   provided as a single agent or in combination with another pharmaceutical agent in a newly diagnosed leukemia pediatric patient, to maintain remission, or in a relapsed/refractory leukemia pediatric patient.

5. The method of claim 1, wherein the patient is relapsed/refractory to another tyrosine kinase inhibitor or chemotherapy.

* * * * *